(12) United States Patent
De Sousa

(10) Patent No.: US 8,110,400 B2
(45) Date of Patent: Feb. 7, 2012

(54) CULTURE OF MAMMALIAN PLURIPOTENT STEM CELLS IN THE PRESENCE OF HYALURONAN INDUCES DIFFERENTIATION INTO MULTI-LINEAGE PROGENITOR CELLS

(75) Inventor: Paul A. De Sousa, Edinburgh (GB)

(73) Assignee: Roslin Foundation, Roslin (GB)

( * ) Notice: Subject to any disclaimer, the term of this patent is extended or adjusted under 35 U.S.C. 154(b) by 718 days.

(21) Appl. No.: 11/817,652

(22) PCT Filed: Mar. 3, 2006

(86) PCT No.: PCT/GB2006/000800
§ 371 (c)(1),
(2), (4) Date: Aug. 12, 2008

(87) PCT Pub. No.: WO2006/092633
PCT Pub. Date: Sep. 8, 2006

(65) Prior Publication Data
US 2009/0123430 A1  May 14, 2009

(30) Foreign Application Priority Data
Mar. 3, 2005  (GB) .................................. 0504427.6

(51) Int. Cl.
*C12N 15/02* (2006.01)
(52) U.S. Cl. ......................... 435/377; 435/383; 435/395
(58) Field of Classification Search .................. None
See application file for complete search history.

(56) References Cited

U.S. PATENT DOCUMENTS
2007/0280989 A1 * 12/2007 Shahar et al. ................. 424/423

FOREIGN PATENT DOCUMENTS
WO    WO-2004/063364 A    7/2004

OTHER PUBLICATIONS

Kavalkovich et al. Chondrogenic Differentiation of Human Mesenchymal Stem Cells within an Alginate Layer Culture System. In Vitro Cell. Dev. Biol.—Animal, 2002, vol. 38, pp. 457466.*
Heins et al. Derivation, Characterization, and Differentiation of Human Embryonic Stem Cells, Stem Cells, 2004, vol. 22, pp. 367-376.*
Pittenger et al. Multilineage Potential of Adult Human Mesenchymal Stem Cells, Science, 1999, vol. 284, pp. 143-147.*
Vogel, G. "Wisconsin to Distribute Embryonic Cell Lines," Science, 287(5455):948-949 (Published Feb. 11, 2000) (Available online at http://www.sciencemag.org/cgi/content/full/287/5455/948) (3 Pages).
Vogel, G. "Researchers get green light for work on stem cells." Science, 289(5484):1442-1443 (Published Sep. 1, 2000) (Available online at http://www.sciencemag.org/cgi/content/full/289/5484/1442) (3 pages).
Amit, et al., Human Feeder Layers for Human Embryonic Stem Cells, Biol. Reprod. 2003; 68(6):2150-2156.
Amit, et al., Feeder Layer- and Serum-Free Culture of Human Embryonic Stem Cells, Biol. Reprod. 2004, 70(3):837-845.
Brown and Papaioannou, Ontogeny of Hyaluronan Secretion During Early Mouse Development, Development 1993; 117: 483-492.
Camenisch, et al., Disruption of Hyaluronan Synthase-2 Abrogates Normal Cardiac Morphogenesis and Hyaluronan-Mediated Transformation of Epithelium to Mesenchyme, J Clin Invest 2000; 106: 349-360.
Camenisch, et al., Heart-Valve Mesenchyme Formation is Dependent on Hyaluronan-Augmented Activation of ErbB2-ErbB3 Receptors, Nat. Med. 2002; 8: 850-855.
Chung, et al., Embryonic and Extraembryonic Stem Cell Lines Derived from Single Mouse Blastomeres, Nature 2006; 439(7073): 216-219.
Conley, et al., Derivation, Propagation and Differentiation of Human Embryonic Stem Cells, Int J Biochem Cell Biol. 2004; 36(4): 555-567.
Gerrard, et al., Differentiation of Human Embryonic Stem Cells to Neural Lineages in Adherent Culture by Blocking Bone Morphogenetic Protein Signaling, Stem Cells 2005; 23: 1234-1241.
Hardingham and Muir, The Specific Interaction of Hyaluronic Acid with Cartilage Proteoglycans, Biochem. Biophys. Acta. 1972; 279(2): 401-405.
Hardwick, et al., Molecular Cloning of a Novel Hyaluronan Receptor That Mediates Tumor Cell Motility, J. Cell. Biol. 1992; 117(6):1343-1350.
Isacke and Yarwood, The Hyaluronan Receptor, CD44, Int. J. Biochem. Cell. Biol. 2002; 34: 718-721.
Itskovitz-Eldor, et al., Differentiation of Human Embryonic Stem Cells into Embryoid Bodies Comprising the Three Embryonic Germ Layers, Mol. Med. 2000; 6(2):88-95.
Jalkanan, et al., Human Lymphocyte and Lymphoma Homing Receptors, Annu. Rev. Med. 1987; 38:467-476.
Keller, In Vitro Differentiation of Embryonic Stem Cells, Curr. Opin. Cell. Biol. 1995; 7(6): 862-869.
Locci, et al., Transforming Growth Factor $\beta_1$-Hyaluronic Acid Interaction, Cell. Tissue. Res. 1995; 281: 317-324.
Meissner and Jaenisch, Generation of Nuclear Transfer-Derived Pluripotent ES Cells from Cloned Cdx2-Deficient Blastocysts, Nature 2006; 439(12): 212-215.
Okamoto, et al., Clonal Heterogeneity in Differentiation Potential of Immortalized Human Mesenchymal Stem Cells, Biochem. Biophys. Res. Commun. 2002; 295: 354-361.
Radomsky, et al., Potential Role of Fibroblast Growth Factor in Enhancement of Fracture Healing, Clin. Orthop. 1998; 355S: S283-293.

(Continued)

*Primary Examiner* — Deborah Crouch
(74) *Attorney, Agent, or Firm* — Law Office of Salvatore Arrigo and Scott Lee, LLP

(57) ABSTRACT

A method for the differentiation of mammalian pluripotent stem (PS) cells into a mortal multi-lineage progenitor cell population is provided which comprises culturing the pluripotent stem cells in the presence of Hyaluronan (HA). The mortal multi-lineage progenitor cell population may be a population of mesenchymal stem cells. The mortal multi-lineage progenitor cell population may form cells of the mesodermal lineage, suitably osteoblasts. Alternatively, the mortal multi-lineage progenitor cell population may form cells of the endodermal lineage or of the ectodermal lineage, which may be neuronal progenitors.

17 Claims, 12 Drawing Sheets

OTHER PUBLICATIONS

Figure 1:
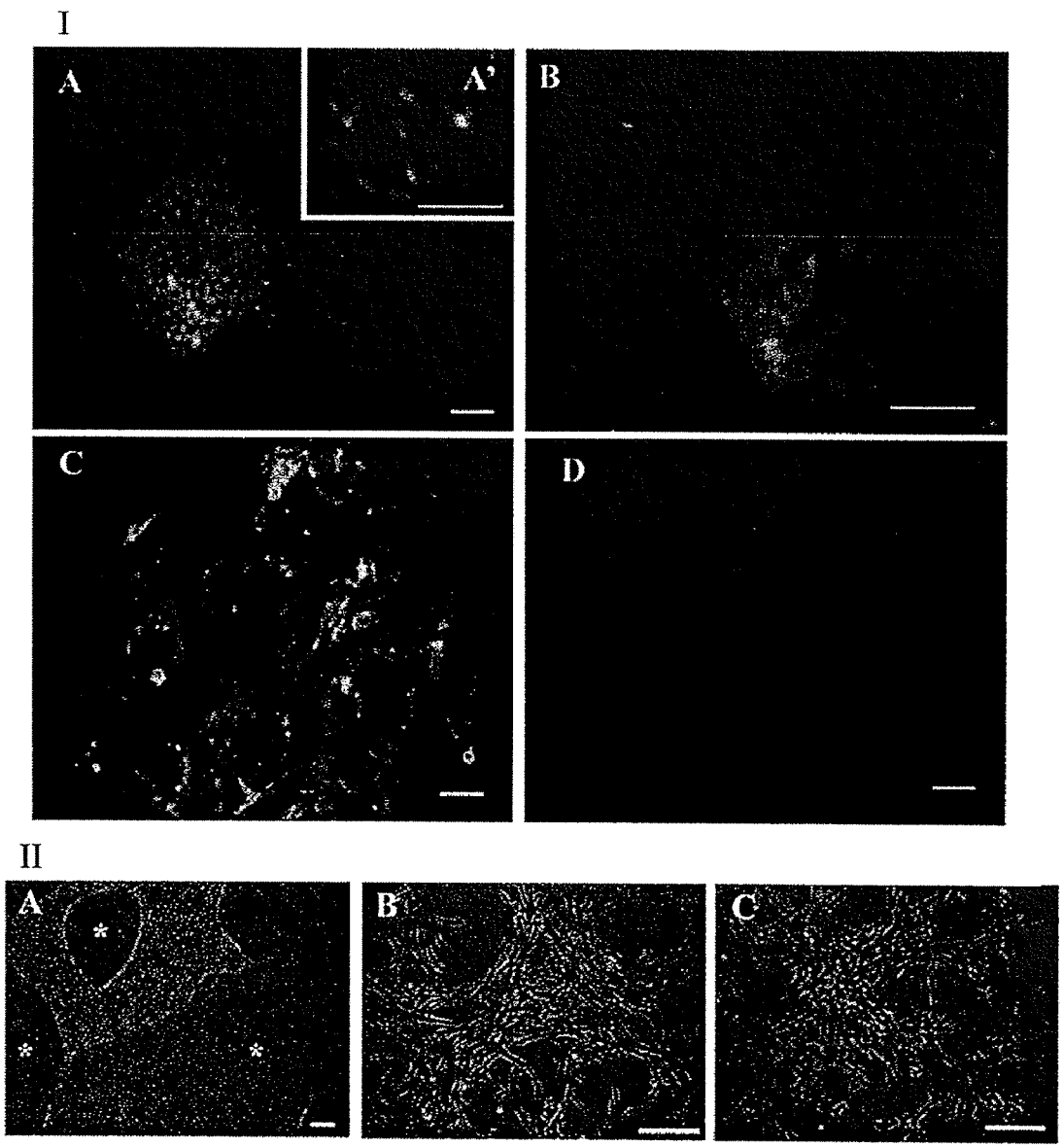

Richards, et al., Human Feeders Support Prolonged Undifferentiated Growth of Human Inner Cell Masses and Embryonic Stem Cells, Nat. Biotechnol. 2002; 20(9): 933-936.

Rosler, et al., Long-Term Culture of Human Embryonic Stem Cells in Feeder-Free Conditions, Dev. Dyn. 2004; 229(2): 259-274.

Schumacher, et al., Staurosporine is a Potent Activator of Neuronal, Glial, and "CNS Stem Cell-Like" Neurosphere Differentiation in Murine Embryonic Stem Cells, Mol. Cell. Neurosci. 2003; 23(4): 669-680.

Sottile, et al., In Vitro Osteogenic Differentiation of Human ES Cells, Cloning & Stem Cells 2003; 5(2): 149-155.

Uchida, et al., Direct Isolation of Human Central Nervous System Stem Cells, Proc. Nat. Acad. Sci. USA 2000; 97(26): 14720-14725.

Verfaillie, Adult Stem Cells: Assessing the Case for Pluripotency, Trends in Cell. Biol. 2002; 12(11): 502-508.

Xu, et al., Feeder-Free Growth of Undifferentiated Human Embryonic Stem Cells, Nat. Biotech. 2001; 19: 971-974.

Zhang, et al., Generation of Oligodendroglial Progenitors from Neural Stem Cells, J. Neurocytol. 1998; 27(7): 475-489.

Ventura, et al.., Butyric and Retinoic Mixed Ester of Hyaluronan: A Novel Differentiating Glycoconjugate Affording a High Throughput of Cardiogenesis in Embryonic Stem Cells, J. Biol. Chem. 2004; 279(22): 23574-23579.

Wheatley, et al., Induction of a Hyaluronan Receptor, CD44, During Embryonal Carcinoma and Embryonic Stem Cell Differentiation, Cell Adhesion and Communication 1995; 3(3): 217-230.

* cited by examiner

CULTURE OF MAMMALIAN PLURIPOTENT STEM CELLS IN THE PRESENCE OF HYALURONAN INDUCES DIFFERENTIATION INTO MULTI-LINEAGE PROGENITOR CELLS

FIELD OF INVENTION

The present invention relates to methods for the differentiation of pluripotent stem cells into mortal cells, which retain the potential to form adult cell lineages.

BACKGROUND OF THE INVENTION

A stem cell is defined as a self-renewing primitive cell that can divide indefinitely (i.e. it is immortal) and can develop into functional, differentiated cells. Differentiated cells are of value for the treatment of degenerative disease or injury by transplantation, or as in vitro model systems for pharmaceutical or toxicology screening. A limitation of differentiated cells however, is their limited capacity to proliferate in culture.

Stem cells can be derived from embryonic, fetal and adult tissue, with embryo stem cells exhibiting the greatest capacity for immortal self-renewal (i.e. expansion), and pluripotency to form differentiated cells. However, the immortal character of stem cells when undifferentiated can result in the formation of tumours if transplanted into a living organism. This is a critical problem for the use of stem cells in the treatment of degenerative diseases or injuries such as for example Parkinson's disease, diabetes, spinal cord repair, or bone repair, etc. Therefore what is needed are methods to control the immortality of cells without compromising their useful proliferative capacity and their lineage potential. That is, what is needed is to re-create a proliferative but mortal population of cells, similar to mesenchyme, which forms during embryo gastrulation, whose lineage potential is retained and controlled by local microenvironments.

Immortal stem cell self-renewal can be accomplished in vitro by growth of cells on either differentiated helper/feeder cells or under feeder-free conditions on extracellular matrix substrates by supplementation of media with defined growth factors or cytokines. For example, human embryo stem cells (hESCs) can be self-renewed by growth in feeder-free culture system consisting of growth on Matrigel™ (MG), a commercially available matrix derived from mouse tumours containing mostly laminin, collagen IV, and heparin sulfate proteoglycan) (Xu et al., 2001). Growth of hESCs on this matrix still requires prior conditioning of culture medium by feeder cells and supplementation with bFGF. Under these conditions laminin could also support hESC self-renewal, whereas other extracellular matrix (ECM) molecules such as Fibronectin and Collagen could not (Xu et al., 2001). However, hESC interactions with the ECM may be growth factor dependent since Fibronectin can support hESC self-renewal provided that the medium is further supplemented with transforming growth factor β1 (TGFβ1) and Leukemia inhibitory Factor (LIF) in addition to bFGF (Amit M et al., 2004).

The first ES cell lines derived from either non-human primates or humans were obtained using medium containing bovine fetal serum and mitotically inactivated mouse embryonic fibroblasts (MEF) as supporting feeder layers (1, 2). Prior to this, derivation of hES without feeders resulted in uncontrolled cell differentiation with successive passages (3). Recently, it has become possible to maintain hES in an undifferentiated state by relying instead on MEF conditioned medium and cultivation on the extra-cellular matrix (ECM) molecule laminin alone or with collagen, and heparan sulfate in a matrigel matrix (4). Medium conditioned by mouse embryonic or human adult fibroblasts or epithelial cells immortalized with hTERT cannot prevent hES from differentiating, despite growth on ECM substrates (4). Thus, one or more factors secreted by feeder cells, such as mouse embryo-derived fibroblasts, uniquely contribute to hES cell maintenance on ECM substrates.

Stem cell differentiation can be mediated in vitro by a variety of methods involving culture of cells that are adherant to a substrate or in suspension. For example:

- Indirect embryoid body mediated differentiation of cell representative of all germinal lineages (endoderm, ectoderm, mesoderm) (Keller, 1995; Itskovitz-Eldor et al., 2000; Conley et al., 2004)
- Directed differentiation of neural cells by suspension culture of neurospheres (Zhang et al., 1998; Uchida et al., 2000; Schumacher et al., 2003)
- Differentiation of cells grown on differentiated helper/feeder cells (Richards et al., 2002; Amit et al., 2003; Amit et al., 2004)
- Differentiation of cells grown on specified extracellular matrix molecules (Xu et al., 2001; Rosler et al., 2004)

The problem with all of these strategies is that they favour either a heterogeneous or single population of terminally differentiated cell phenotypes whose proliferative capacity is lost. What is needed is a method for the controlled differentiation of an intermediate progenitor population with proliferative capacity that retains its potential to yield a single lineage in response to specific environmental cues. In animal development cells that conceptually possess such properties evolve during the process of gastrulation, which results in the formation of three primary germ layers, ectoderm, mesoderm, and endoderm. Of these layers, mesenchymal cells derived from the mesoderm layer have the unique capacity to proliferate and migrate to specific sites, in developing organisms referred to as limb buds, at which they become terminally differentiated and normally give rise to muscle, skeletal (i.e. bone), blood, vascular and urogenital systems and connective tissue, specifically osteoblasts, chondroblasts, adipocytes, fibroblasts, cardiomyoctes and skeletal myoblasts.

In the adult, mesenchymal cells can be recovered from bone marrow. These are referred to as mesenchymal stem cells because they can be cultured ex-vivo for a limited number of passages and be differentiated at the single cell level into mesodermal cell types as described. When introduced in vivo bone mesenchymal cells can differentiate into the same array of cell types, as well as cells with characteristics of cells outside the mesoderm, including endothelium, neuroectoderm, and endoderm (reviewed in Verfaillie et al. 2002). The formation of mesenchyme during gastrulation in the embryo, or in bone marrow during development or in the adult organism, is a complex process mediated by the interaction of a broad range of soluble and insoluble factors, which include amongst others glycosominoglycans. The complexity of this process is such however, that it is unlikely that a single factor could yield the unique properties of mesenchymal cells.

Glycosaminoglycans (GAGs) are unbranched chains composed of repeating disaccharide units. These disaccharide units always contain an amino sugar (N-acetylglucosamine or N-acetylgalactosamine), which in most cases is sulfated, with the second sugar usually being a uronic acid (glucuronic or iduronic). GAGs are highly negatively charged because of the presence of carboxyl or sulfate groups on most of their sugar residues. As such they are strongly hydrophilic. GAGs tend to adopt highly extended conformations and form matrices that are space filling and resistant to compressive forces. Four main groups of GAGs have been distinguished by their sugar residues, the type of linkage between these residues, and the number and location of sulfate groups. They include: (1) hyaluronan, (2) chondroitin sulphate and dermatan sulfate, (3) heparan sulfate and heparin, and (4) keratan sulfate.

Hyaluronan (also called hyaluronic acid or hyaluronate) is the simplest of GAGs. It consists of a regular repeating sequence of non-sulfated disaccharide units, specifically N-acetylglucosamine and glucuronic acid. Its molecular weight can range from 400 daltons (the disaccharide) to over a million daltons. It is found in variable amounts in all tissues, such as the skin, cartilage, and eye, and in most if not all fluids in adult animals. It is especially abundant in early embryos. Space created by hyaluronan, and indeed GAGs in general, permit it to play a role in cell migration, cell attachment, during wound repair, organogenesis, immune cell adhesion, activation of intracellular signalling, as well as tumour metastasis. These roles are mediated by specific protein and proteoglycan binding to Hyaluronan. Thus, in articular cartilage, hyaluronan and aggrecan form large aggregates important for the function of cartilage (Hardingham and Muir, 1972). Furthermore, cell motility and immune cell adhesion is mediated by the cell surface receptor RHAMM (Receptor for Hyaluronan-Mediated Motility; Hardwick et al., 1992) and CD44 (Jalkenan et al., 1987; Miyake et al., 1990).

Hyaluronan is synthesized directly at the inner membrane of the cell surface with the growing polymer extruded through the membrane to the outside of the cell as it is being synthesized. Synthesis is mediated by a single protein enzyme, hyaluronan synthetase (HAS) whose gene family consists of at least 3 members. By contrast other GAGs are synthesized inside the cell in the Golgi apparatus, possibly in association with some core protein, and then released by exocytosis. Hyaluronan degradation in vertebrate tissues in vivo is mediated by hyaluronidase, and exoglycosidases that remove sugars sequentially Mammalian-type hyaluronidases have both hydrolytic and transglycosidase activities and can degrade hyaluronan and chondroitin as well as, to a small extent, dermatan sulfate.

Human ES cells will have several distinct roles in medicine, for which it is important that lines are available from a variety of different genotypes. Ideally it should be practicable to obtain ES cells with a new specific genotype by their derivation from embryos produced by nuclear transfer. In addition to their potential use in cell therapy, such lines will create new opportunities for studies of drug toxicology, for drug discovery and studies of diseases that have a genetic component, but not necessarily a result of inappropriate function of a single gene. Although human embryonic stem (hES) cell lines show great promise for the development of cell-based therapies to replace damaged tissues, the currently available lines may be of little utility for this purpose. This is because of their provenance. To be used a source of tissue for transplantation in the future, hES cells will have to be derived and maintained under far more stringent conditions of 1) informed consent from the donor and 2) bio-safety, than hitherto observed. Central to bio-safety issues is the capacity to derive and maintain hES cells or their derivatives under defined and pathogen free conditions. This requirement is severely constrained by the dependence of existing protocols on animal feeder cells and undefined factors provided by feeder cells, conditioned medium, or exogenously supplied serum.

It has now been found that Hyaluronan can surprisingly assist in the differentiation of pluripotent stem cells to derive a mortal multi-lineage progenitor cell population which resemble adult mesenchymal stem cells.

SUMMARY

According to a first aspect of the invention, there is provided a method for the differentiation of mammalian pluripotent stem (PS) cells into a mortal multi-lineage progenitor cell population, comprising culturing the pluripotent stem cells in the presence of Hyaluronan (HA).

Such in vitro methods of differentiation provide a mortal multi-lineage progenitor whose terminal differentiation may be dictated by local microenvironment more readily than embryo stem cells. The mortal multi-lineage progenitor cell population may be a population of mesenchymal stem cells. Suitably, the mortal multi-lineage progenitor cell population may have the capacity to form mesodermal lineages, including bone (i.e. osteoblasts), cartilage (i.e. chondroblasts), fat (i.e. adipocytes), connective tissue (i.e. fibroblasts), muscle (i.e. myoblasts or cardiomyocytes), as well as the plasticity to form ectoderm (i.e. epithelial cells, neurons) or endoderm (i.e. hepatocytes, pancreatic islet cells) lineages when cultured subsequently with at least one appropriate stem cell growth factor.

Mesenchymal cells may be characterised by expression of the following markers; CD71, CD90, GATA6, Nodal, BMP-2. Additional markers include, but are not restricted to BMPR-IA/ALK-3, BMPR-IB/ALK-6, BMPR-II, Endoglin/CD105, Nucleostemin, Sca-I, SCF R/c-kit, STRO-1, VCAM-1.

The process of differentiation of mesenchymal cells into adipocytes, chondrocytes, myocytes, and osteocytes may be characterised by expression of specific markers. Adipogenesis markers include PPARG, Adiponectin/Acrp30, FABP4, Glut4, Leptin. Chondrogenesis markers include SOX9, Collagen 2 (i.e. COL2), COL10, MMP13, Aggrecan, DSPG3. Myogenesis markers include FABP3, GATA-4, NKX2.5, Pax3, Pax7, delta-Sarcoglycan, alpha-Smooth Muscle Actin, Troponin T. Osteogenesis markers include Alkaline Phosphatase, CBFA1/RUNX2, Collagen I, Decorin, Fibronectin, Osteoadherin, Osteocalcin, SPARC, Thrombopoietin, PTHR1, PTHR2.

Mesenchymal stem cell growth factors include BMPs (Bone Morphogenetic Proteins), EGF Family, GDFs (Growth Differentiation Factors), IGF Family, VEGF/PDGF Family. The BMPs (Bone Morphogenetic Proteins) include BMP-2, BMP-3, BMP3b/GDF-10, BMP-4, BMP-5, BMP-6, BMP-7, BMP-8, BMP-15 and Decapentaplegic.

The IGF family includes IGF ligands such as IGF-I and IGF-II, the IGF-I Receptor (CD221), the IGF Binding Protein (IGFBP) Family which includes ALS, CTGF/CCN2, Endocan, IGFBP-1, IGFBP-2, IGFBP-3, IGFBP-4, IGFBP-5, IGFBP-6, IGFBP-rp1/IGFBP-7 and NOV/CCN3.

The EGF family includes the EGF ligands which include Amphiregulin, Betacellulin, EGF, Epigen, Epiregulin, HB-EGF, Neuregulin-3, NRG-isoform GGF2, NRG1-isoform SMDF, NRG1-alpha/HRG1-alpha, NRG1-beta1/HRG1-beta 1, TGF-alpha, TMEFF1/Tomoregulin-1, TMEFF2. The EGF family also includes the EGF R/ErB receptor family which includes EGF R, ErbB2, ErbB3 and ErbB4.

The VEGF/PDGF family includes Neuropilin-1, Neuropilin-2, PDGF, PDGF R alpha, PDGF R beta, PDGF-A, PDGF-B, PDGF-C, PDGF-D, PDGF-AB, PIGF, VEGF R1/Flt-1, VEGF R2/Flk-1, VEGF R3/Flt-4, VEGF, VEGF-B, VEGF-C and VEGF-D.

The GDFs (Growth Differentiation Factors) family includes GFD-1, GDF-3, GDF-5, GDF-6, GDF-7, GDF-8, GDF-9, GDF-11, GDF-15.

Embryonic stem cell markers include ABCG2, Alkaline phosphatase, E-Cadherin, CCR4, CD9, Cripto, DPPA5/

ESG1, FGF-4, FGF R4, FoxD3, FoxP3, GDF-3, Integrin alpha 6/CD49f, Integrin beta 1/CD29, Lefty, Nanog, Oct 3/4, Podocalyxin, SOX2, SPARC, SSEA-1, SSEA-3, SSEA-4, STAT3.

Early ectodermal lineage markers include Nestin, Otx2, TP63/TP73L, beta-III Tubulin, SHH, and PAX6. Ectoderm has the potential to form cell types such as neurons and early neuronal lineage markers include ACE, ALCAM, CD90/Thy1, GAD1/GAD67, Glut1, MAP2, NCAM-L1, Nectin-2/CD112, NeuroD1, NF-L, NF-M, ROBO3, gamma-Secretase, alpha-Secretase, beta-Secretase, beta-III tubulin, Tyrosine Hydroxylase. Neural stem cell markers include ABCG2, CXCR4, FGF R4, Frizzled-9, Musashi-1, Nestin, Noggin, Nucleostermin, Prominin 2, SOX2, Vimentin.

Neural stem cell growth factors include Activins, ALKs (Activin Receptor-like Kinases, BNPs, EGF family, FGF family, GDFs, Hedgehog family, IGF family, VEGF/PDGF family, Wnt-related family as described herein.

Early endodermal lineage markers include those for definitive endodemm such as FABP1, FABP2, GATA-4, HNF-3 beta, as well as those markers for primitive endoderm such as alpha-Fetoprotein, beta-Catenin, GATA-4, SOX17 and SOX7.

Early mesodermal cell markers include Brachyury, Cryptic and FABP4.

Markers for primordial germ cells include early primordial germ cell markers such as GCNF/NR6A1, Oct-3/4 and SSEA-1, as well as late primordial germ cell markers such as FABP9, Stella/Dppa3 and VASA.

Other markers are as described in the Examples contained herein.

Further differentiation into ectodermal cells can suitably be achieved by culturing progenitor cells in a culture medium comprising BMP/GDF-9.

Further differentiation into endodermal cells can suitably be achieved by culturing progenitor cells in a culture medium comprising wnt.

Further differentiation into mesodermal cells can suitably be achieved by culturing progenitor cells in a culture medium comprising Activin, Nodal and/or TGF-β.

Other differentiation protocols are as described in the Examples contained herein.

The invention applies to cells of an embryonic or adult origin in mammals, both human and non-human mammals, including but not limited to human and non-human primates, ungulates, ruminants and rodents. Ungulate species include, but are not limited to, cattle, sheep, goats, pigs, horses. Rodent species include, but are not limited to, rats and mice. The invention may also find application in other mammalian species such as rabbits, cats and dogs.

Examples of preferred pluripotent stem cell populations which can be differentiated according to the present invention include primate pluripotent stem (pPS) cells, such as human pluripotent stem (hPS) cells. Such cells include adult human mesenchymal cells. However, the invention may have its greatest application in the differentiation of cells derived from embryonic or fetal sources.

Cells derived from embryonic sources may include embryonic stem cells or stem cell lines obtained from a stem cell bank or other recognised depository institution. Other means of producing stem cell lines include the method of Chung et al (2006) which comprises taking a blastomere cell from an early state embryo prior to formation of the blastocyst (at round the 8-cell stage). The technique corresponds to the pre-implantation genetic diagnosis technique routinely practised in assisted reproduction clinics. The single blastomere cell is then co-cultured with established ES-cell lines and then separated from them to form fully competent ES cell lines.

Another procedure is that of Meissner & Jaenisch (2006), in which the cdx2 gene is silenced in the donor nucleus during the process of nuclear transfer to prepare a reconstructed embryo from which a line of ES cells is derived. The cdx2 gene is turned back on in the isolated blastocyst cell taken from the embryo which is used to prepare the cell line. This is an example of, so-called, "Alternative Nuclear Transfer" where the embryo is not capable of implantation but the ES cell line derived therefrom is fully competent.

A pluripotent stem (PS) cell includes an embryonic stem cell. Pluripotent stem (PS) cells also include pluripotent cells which arise from the further division of totipotent cells that are capable of developing into any other cell type in the adult body but which do not have the potential to develop into an entire body.

A key advantage of the methods of the present invention is the fact that HA induces differentiation of a proliferative and mortal cell population of mesodermal derived cell-types whose potential includes (but is not limited to) the formation of osteoblasts, neurons, hepatocytes, germ cells, myocytes and cardiomyocytes, and which potential is retained for an extended period. This should benefit therapeutic strategies involving the transplantation of osteoblasts by minimising the potential for transmission of teratoma forming undifferentiated cells.

Hyaluronan is an extracellular matrix glycosoaminoglycan molecule that has not been considered to date in the context of hESC culture. HA (also called hyaluronic acid or sodium hyaluronate) is the simplest type of Glycosaminoglycan (GAG), consisting of up to 25,000 unbranched repeating non-sulfated disaccharide units ($M_r$ 401), specifically N-acetyl-glucosamine and glucuronic acid. Accordingly, it can exist in both low ($M_r$ 1500-5000) and high ($M_r$>10,000) molecular weight forms. In addition to being found in variable amounts in all adult tissues, such as the skin, cartilage, and eye, it is also a predominant feature of embryonic ECM, especially during epiblast formation and embryo outgrowth, and in vivo provides the necessary microenvironment for undifferentiated cell expansion (Brown and Papaioannou, 1993). References to Hyaluronan (HA) therefore include references to Hyaluronic acid, Sodium Hyaluronate, or Hyaluronate disaccharide, and may be used interchangeably unless the context clearly specifies otherwise.

As a large negatively charged macromolecule with viscoelastic properties, HA physically provides hydrated matrices that facilitate cell proliferation and migration. These processes are mediated by HA's interactions with a broad range of molecules from lipids and other GAGs, to proteoglycans and proteins. In culture, HA is believed to serve as a reservoir for growth factors, including bFGF, protecting them from tryptic digestion (Locci et al., 1995; Radomsky et al., 1998). Most significantly, HA can modulate growth factor signal transduction via its predominant receptor CD44, also known as the Homing-Cell Adhesion Molecule (H-CAM) for its involvement in mediating cell migration (reviewed in Isacke and Yarwood, 2002). This has been exemplified in a mouse embryonic heart explant model wherein HA augments the transformation of differentiated cardiac endothelial cells into heart-valve mesenchyme via CD44 interaction with ErB2-ErbB3 receptors, and Ras-GTPase signalling (Camenisch et al., 2000; ibid, 2002).

In one embodiment, it may be convenient to use Hyaluronate disaccharide in a range of from 5 µg/ml to 100 µg/ml. optionally of from 10 µg/ml to 50 µg/ml, suitably at 10 µg/ml. The formulation may be made in any convenient diluent, including water, isotonic water, and/or phosphate buffered saline (PBS). Additionally, or alternatively, it may be convenient to use Hyaluronic Acid in a range of from 50 µg/ml to 5 mg/ml, optionally of from 75 µg/ml to 500 µg/ml, suitably at 100 µg/ml. The formulation may be made in any convenient diluent, including water, isotonic water, and/or phosphate buffered saline (PBS).

Other growth factors, chemicals, nutrients may be present as desired in the medium. Such components may include, but are not limited to, vitamins, antibiotics, etc.

The present invention therefore also extends to the use of Hyaluronan as a medium for the differentiation of mammalian pluripotent stem (PS) cells into a mortal multi-lineage progenitor cell population.

Hyaluronan may be used in the form of Hyaluronate disaccharide ($M_r$ 401), specifically N-acetylglucosamine and glucuronic acid, or Sodium Hyaluronate and/or Hyaluronic Acid, in either or both of the low ($M_r$ 1500-5000) and high ($M_r$>10,000) molecular weight forms.

According to a second aspect of the invention, there is provided a population of a mortal multi-lineage progenitor cells differentiated from a population of mammalian pluripotent stem (PS) cells according to a method of the first aspect of the present invention.

According to a third aspect of the present invention, there is provided a system for the differentiation of a population of a mortal multi-lineage progenitor cells, said system comprising a population of mammalian pluripotent stem (PS) cells cultured in the presence of Hyaluronan and a population of mortal multi-lineage progenitor cells differentiated from said PS cells.

Such a system therefore comprises a composition comprising a population of mammalian pluripotent stem (PS) cells cultured in the presence of Hyaluronan and a population of mortal multi-lineage progenitor cells differentiated from said PS cells.

According to a fourth aspect of the present invention, there is provided a method for the treatment of a patient suffering from a degenerative disease or injury, the method comprising the transplantation into said patient of a population of mortal multi-lineage progenitor cells prepared according to a method of the present invention. This aspect of the invention, therefore also extends to such cells for use in transplantation.

Degenerative diseases or injuries that may be treated in accordance with this aspect of the invention, include but are not limited to bone and cartilage repair, Parkinson's disease, diabetes, nerve repair, including spinal cord repair, etc. Embodiments of this aspect of the invention, therefore extend to the use of cells prepared according the present invention in the preparation of a medicament for the treatment of a degenerative disease or injury.

In one embodiment of the invention, there is therefore provided a culture medium comprising Hyaluronan for the differentiation of mammalian pluripotent stem (PS) cells into a mortal multi-lineage progenitor cell population.

The culture medium may be provided in the form of a coating of Hyaluronan for cell attachment. The Hyaluronan may be present as Hylauronan disaccharide (M.Wt. 401.3 D), Sodium Hyaluronate and/or Hyaluronic Acid (M.Wt. 200 kD). The coatings may be applied at around 0.1 ml per cm² for 30 minutes at 4° C., before warming to room temperature, followed by aspiration of excess and transfer of cells. Hyaluronate disaccharide may be applied at 10 µg/ml in PBS and/or Hyaluronic acid at 100 µg/ml. Hyaluronic acid may be applied up to at least around 1 mg/ml if desired, or more if required.

The present invention therefore also extends to articles coated with Hyaluronan, such as tissue culture dishes, multi-well plates (e.g. 1, 2, 4, 8, 24, 48, 96-wells, etc), Petri-dishes, tissue culture flasks, fermentors, bioreactors etc for the differentiation of mammalian pluripotent stem (PS) cells into a mortal multi-lineage progenitor cell population. Such articles ma be composed of any generally suitable material, such as a plastics material, for example polypropylene, or other materials such as glass, metal etc. Suitable metals include mirror-polished metals, e.g. mirror-polished stainless steel.

Preferred features for the second and subsequent aspects of the invention are as for the first aspect mutatis mutandis.

The present invention will now be further described with reference to the following Examples which are present for the purposes of illustration only and are not to be construed as being limiting on the invention. Reference in the Examples is made to a number of drawings in which:

FIG. 1 shows HA and HA receptor expression in hESCs and differentiation after growth on HA/HD or plastic alone. (I) Treatment of both H1 (shown) and H9, with a fluorescently-tagged HA-binding protein specifically stains both undifferentiated colony cells (A) and differentiating cells surrounding each colony (A'), indicative of endogenous HA expression. By immunofluorescence, both cell types in each line are also positive for the HA-binding proteoglycan syndecan, also known as CD138 (B), and the constitutive isoform of the CD44 receptor lacking variant exons, known as CD44s (C). hESCs treated with fluorescently conjugated secondary antibody alone and imaged digitally at the same settings used for HA-binding proteins exhibit negligible staining (D). Bars equal 10 microns. (II) Undifferentiated HESC colonies (see * in A, as shown for H1) can be maintained in mouse embryo fibroblast conditioned media supplemented with bFGF and KOSR if cells are on Matrigel™. However, plating on a substrate of low molecular weight HA (2000 kD; shown B) or Hyaluronan Disachamide induces a fibroblast morphology, comparable to plating on plastic alone (C). Bars equal 10 microns.

Figure 2:
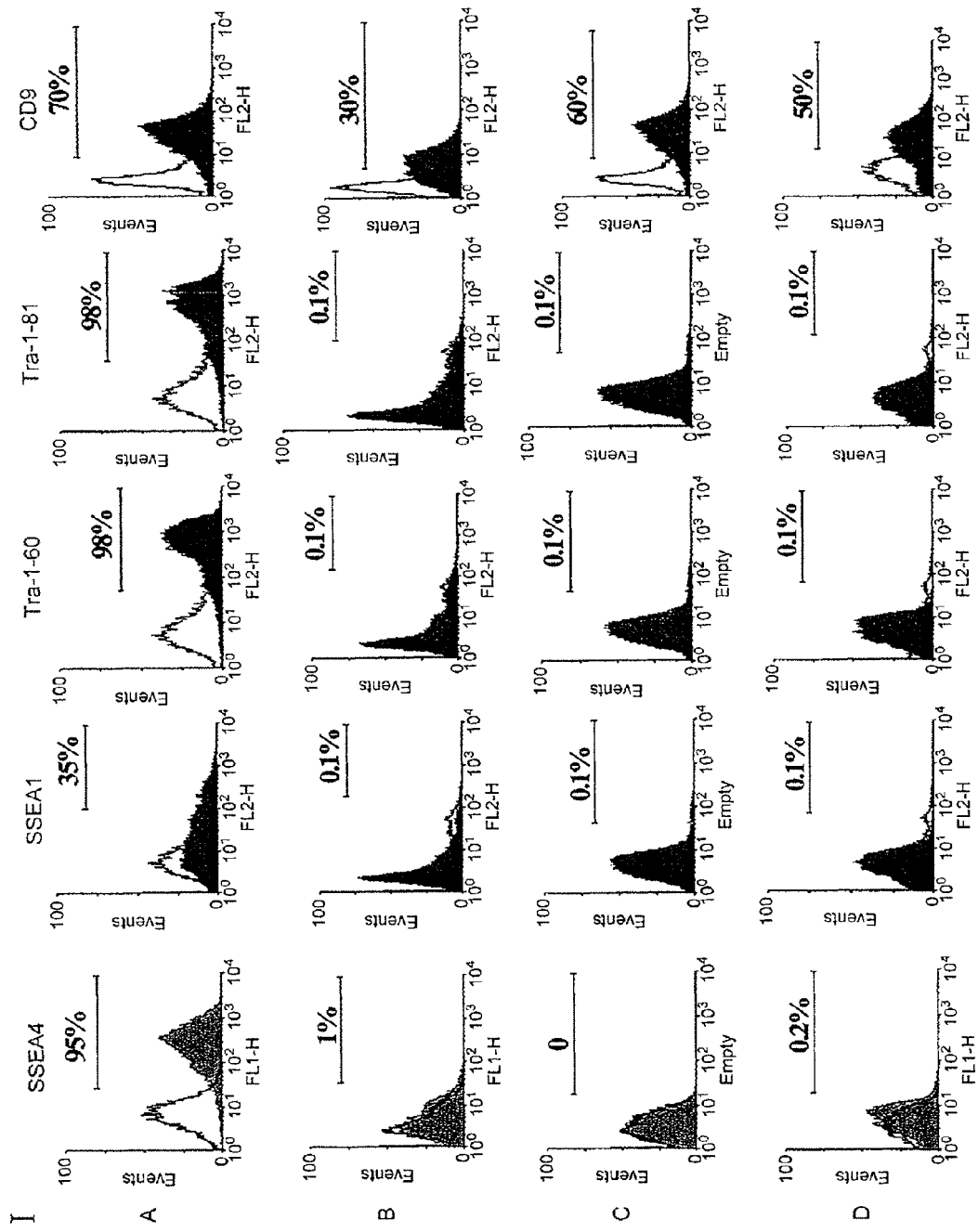
Figure 2:
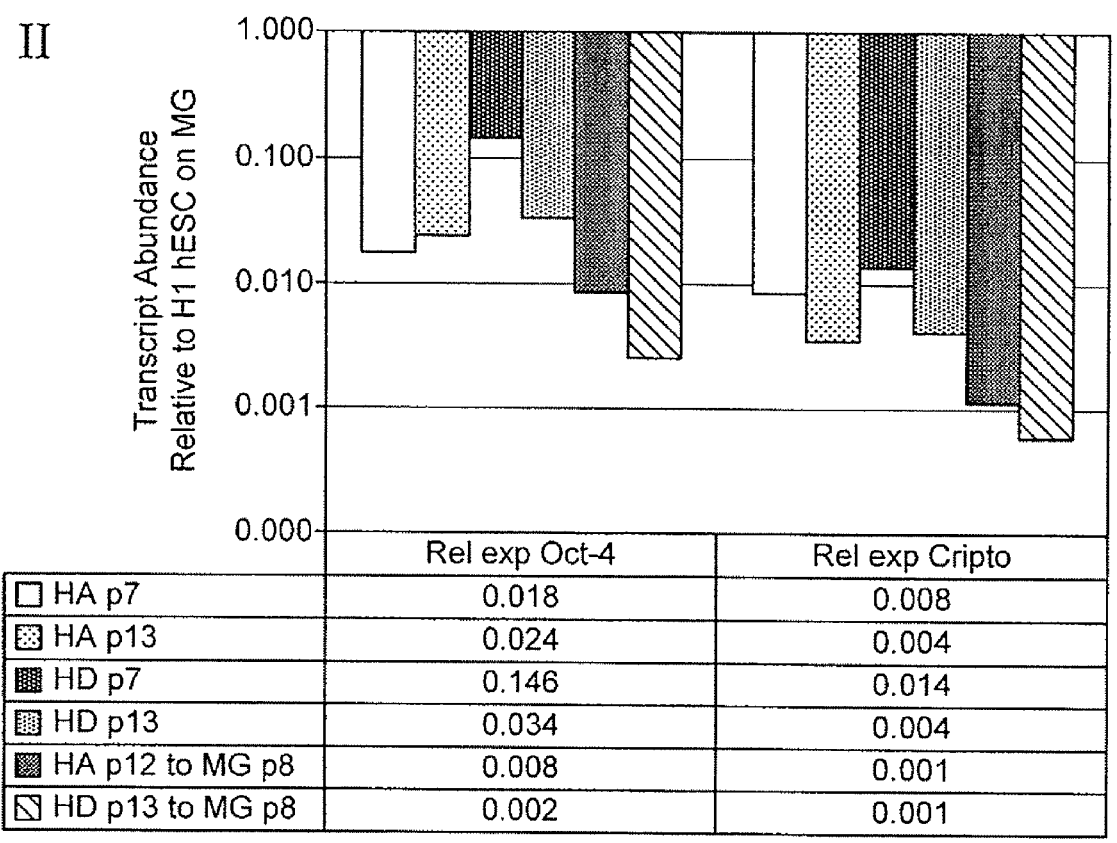
Figure 3:
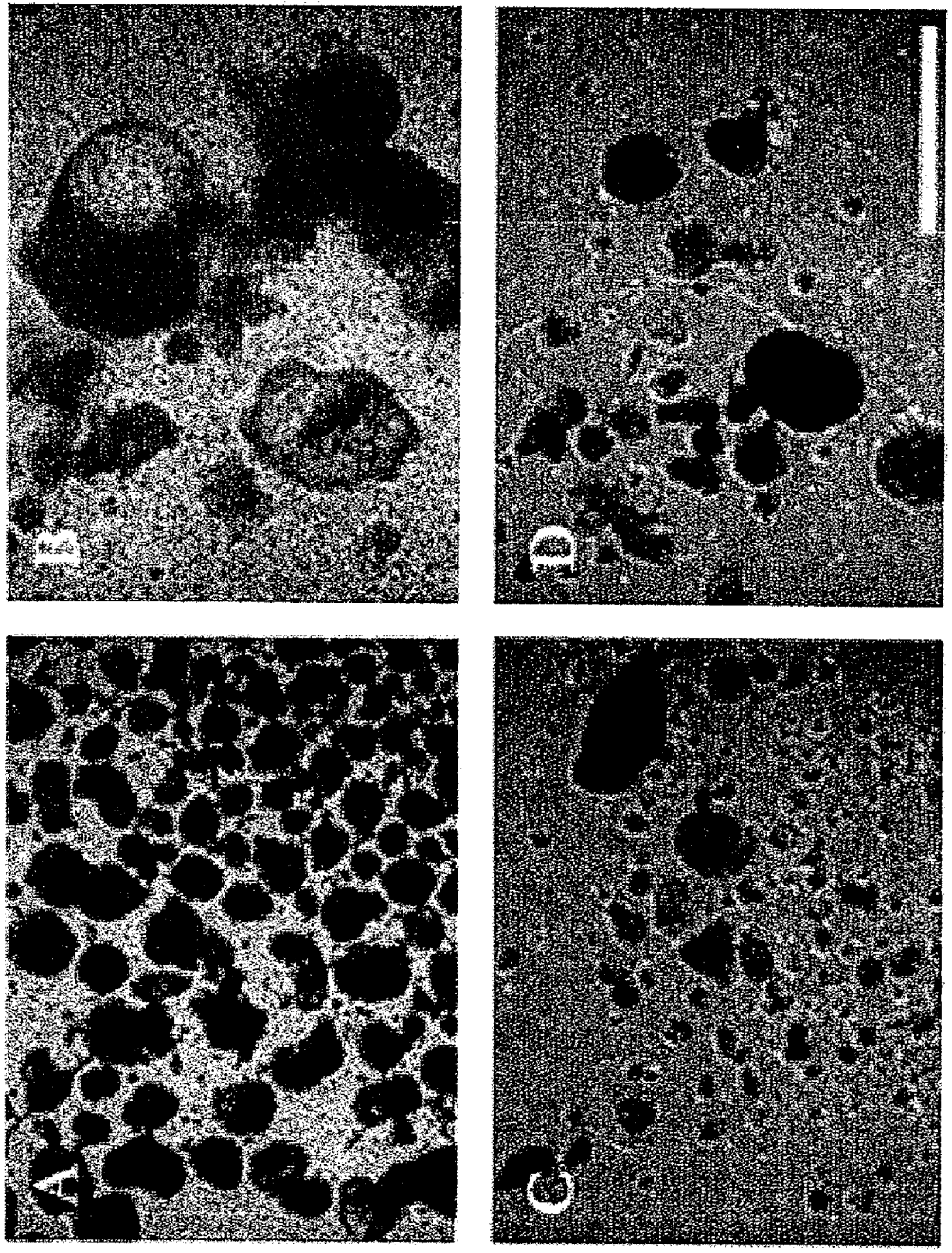

FIG. 2 shoes the loss of undifferentiated hESC markers following growth on Hyaluronan. (I) By Flow cytometry, undifferentiated H1 (shown) or H9 hESC on Matrigel™ are positive for SSEA4, Tra-1-60, Tra-1-81, and CD9, but negative for SSEA-1 (A). By contrast all cell surface markers, with the exception of CD9, are lost following growth on HA (B, @p11), HD (C, @p11), or untreated plastic (D, @p7). (II) By TAQMAN RT-PCR, the abundance of mRNA transcripts for genes associated with hESC pluripotency, namely Oct-4 and Cripto, are reduced following successive passage (p) on HA or HD, relative to growth on Matrigel™. Return to Matrigel™ does not result in a rise in the expression of these genes. The bar indicates the % of the total population of cells positive for the given marker. In all graphs, y-axis is "Events" from 0 to 100; x-axis in the graphs in (A), (B) and (D) is FL1-H, FL2-H, FL2-H, FL2-H, FL2-H from left to right; in (C) the x-axis is "Empty"; for all x-axes the scale reads in gradations of $10^0$, $10^1$, $10^2$, $10^3$ and $10^4$ FIG. 3 shows loss of Embryoid body formation/mediated differentiation post hESC growth on HA/HD. Suspension culture in DMEM+10% FBS of H1 & H9 (shown) hESCs previously maintained in MEFCM/MG form compact aggregates within 2 days (A) and cystic Embryoid Bodies within 4 days (B). By contrast suspension culture of both hESC lines induced to differentiate by growth on HA or HD (shown H9 on HA for 11 passages) form smaller cell aggregates after 2 days (C), which coalesce to form larger dense aggregates that are not cystic after 4 days (D). Formation of dense cellular aggregates which predominates after 10 passages on HA, correlates with loss of potential to form cells which are positive for ectoderm (D-tubulin III), endoderm (α-fetoprotein) and mesoderm (muscle-specific actin) germinal lineage markers (data not shown). Bar equals 100 microns.

Figure 4:
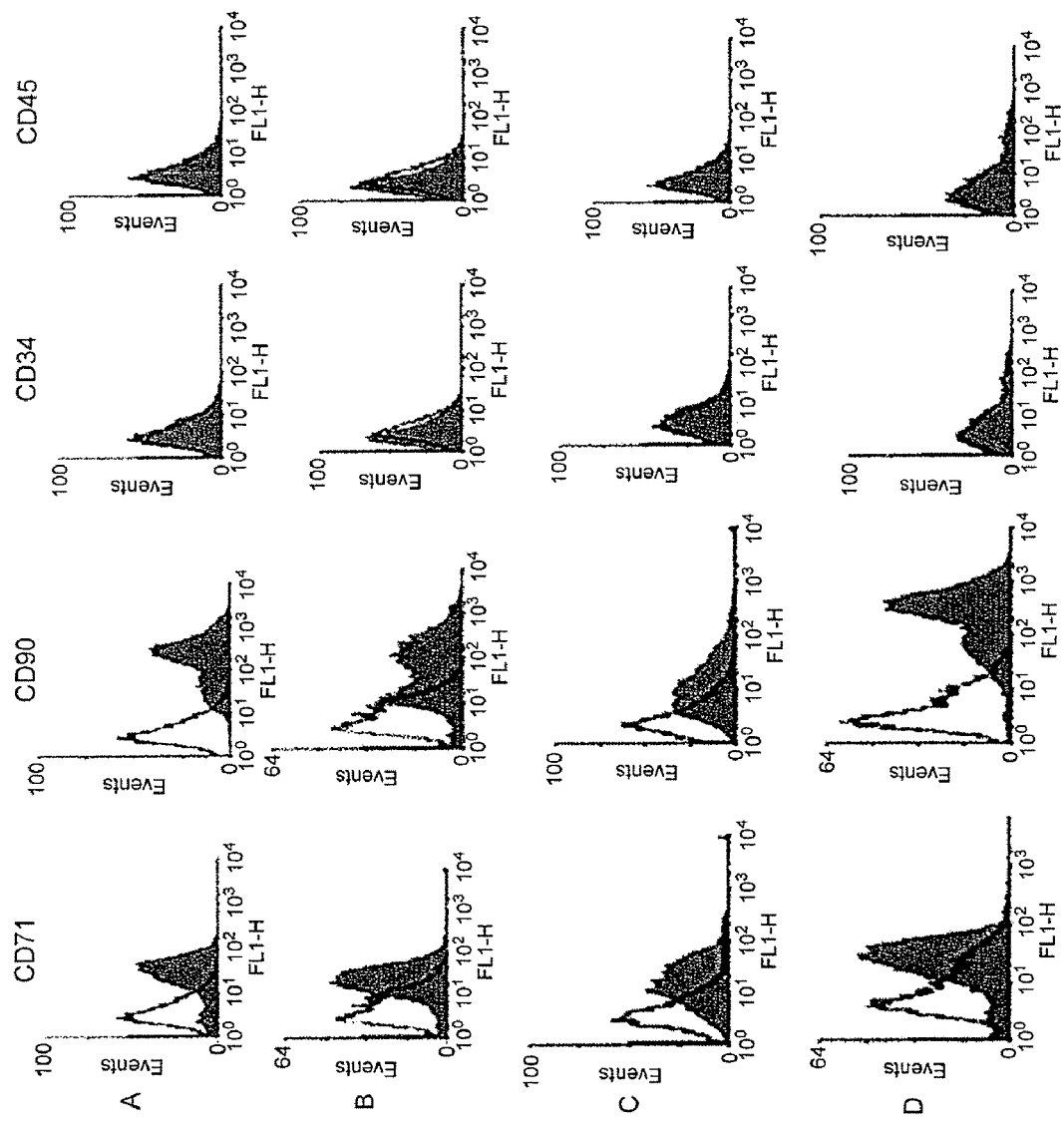

FIG. 4 shows similarities in surface marker expression between undifferentiated and HA-differentiated hESCs with human Mesenchymal Stem Cells (hMSCs) from bone marrow. By flow cytometry, undifferentiated H1 (shown) and H9 hESC grown on Matrigel™ (A), differentiated H1 (B) and H9 (C) grown on HA for 20 or 15 passages, respectively, or hMSC maintained in vitro for 11 passages, are positive for CD71 and 90 and negative for CD34 and 45. In the graphs, the y-axis is "Events" from 0 to 100 (except for the first two graphs in (B) and (D) from the left where the "Events" scale runs from 0 to 64; the x-axis in all the graphs is FL1-H and the scale reads in gradations of $10^0$, $10^1$, $10^2$, $10^3$ and $10^4$.

Figure 5:
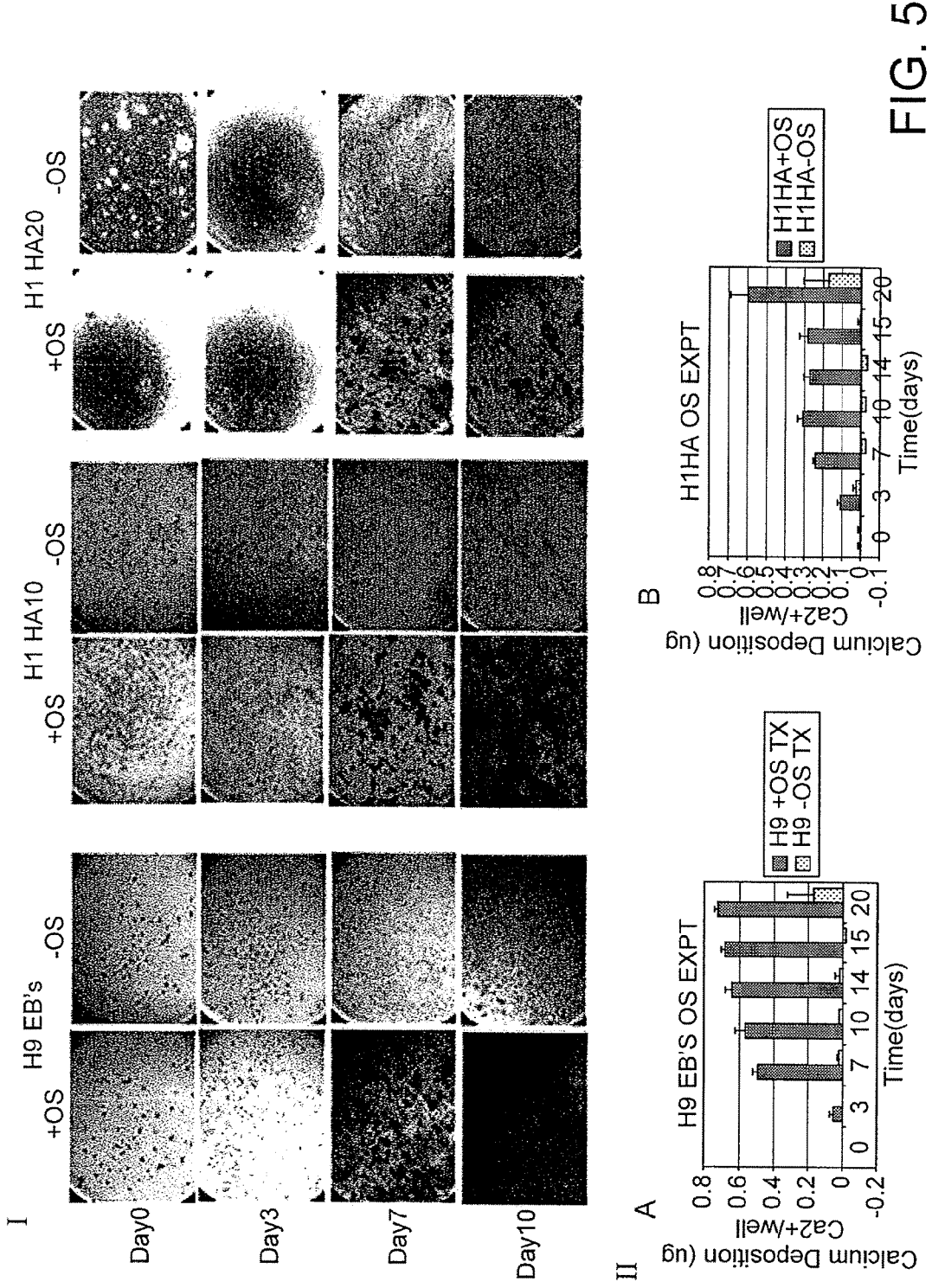

FIG. 5 shows induction of mineralising osteoblasts from HA-differentiated cells. (I) Alizarin Red S staining was used to detect mineralised nodules in H9 embryoid body (EB) derived cells (+ve control) and H1 cells cultured on HA for 10 and 20 passages following 0, 3, 7 and 10 days of culture in the presence or absence of osteogenic supplement (±OS) as previously described (Sottile et al., 2003). In all treatment groups, staining was only observed after 7 days in the presence of OS, with no staining in its absence. (II) Time course over days in culture of calcium deposition in H9 EB (A) and H1-HA for 10 passages B) cells cultured±OS. Data are presented as mean±SEM (n=4)

Figure 6:
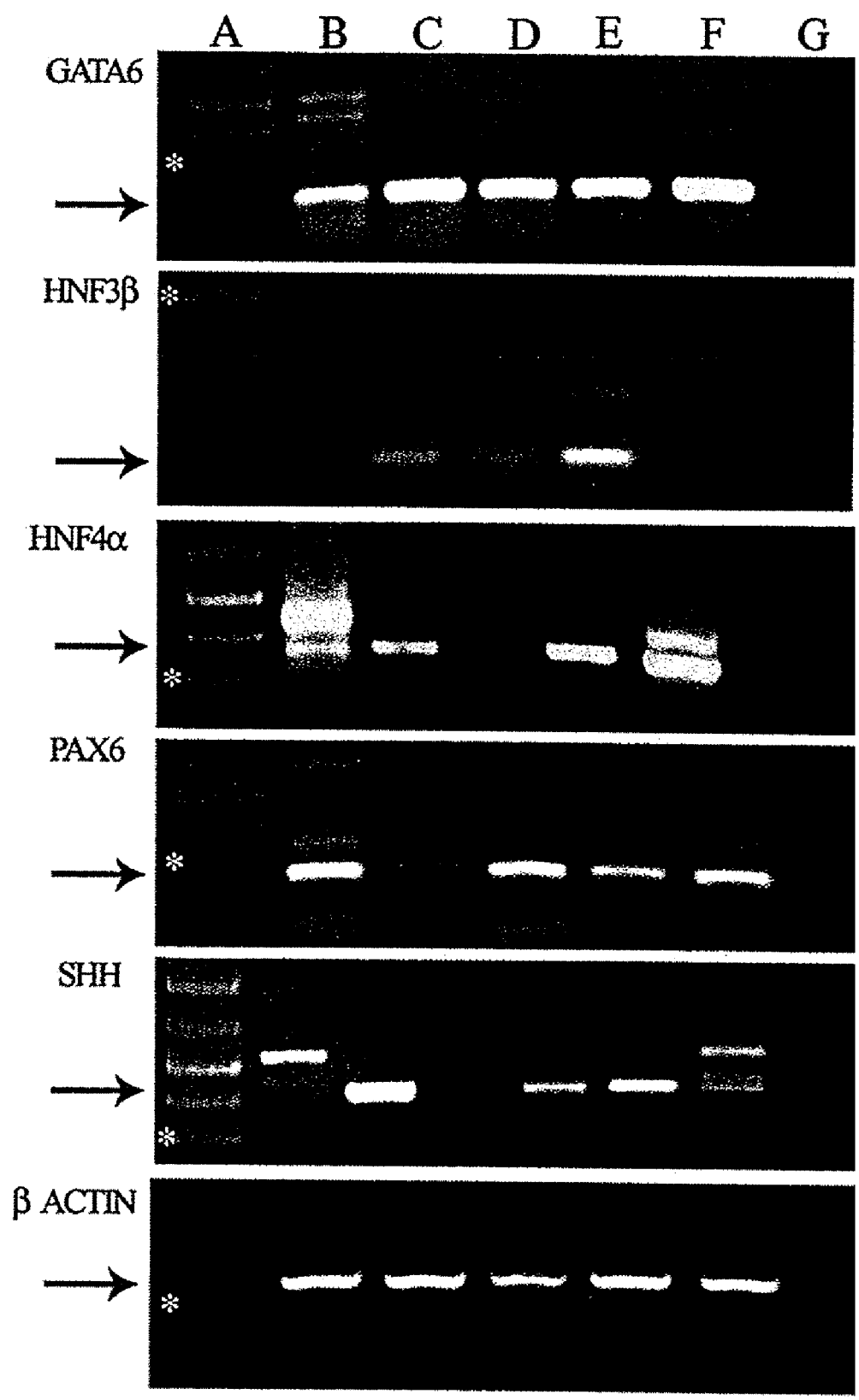

FIG. 6 shows the effect of HA as an hESC substrate. The mRNA detection was by reverse transcription polymerase chain reaction (RT-PCR) of genetic markers for meso/endoderm (i.e. Gata-6), primitive and definitive endoderm (i.e. HNF-3β and HNF-4α), and ectoderm (i.e. PAX-6 and SHH) in H1 hESC cell line. (A) 100 base pair molecular weight marker with asterisk denoting 300 bp band. (B) H1 grown in culture conditions maintaining undifferentiated cell self-renewal involving mouse embryo fibroblast conditioned medium supplemented with 4 ng/ml bFGF on a substrate of Matrigel™ (Xu et al., 2001). (C-E) H1 hESC grown for 10, 15, and 20 passages in the media specified in (A) but on substrate of 100 μg/cm2 HA. (F) Four day suspension cultured embryoid bodies of differentiating H1 hESCs previously maintained in culture conditions specified in (A). These results suggest that despite HA induced differentiation cells still express gene products associated with mesodermal, endodermal and ectodermal lineages, and thus may still harbour the potential to form such lineages.

Figure 7:
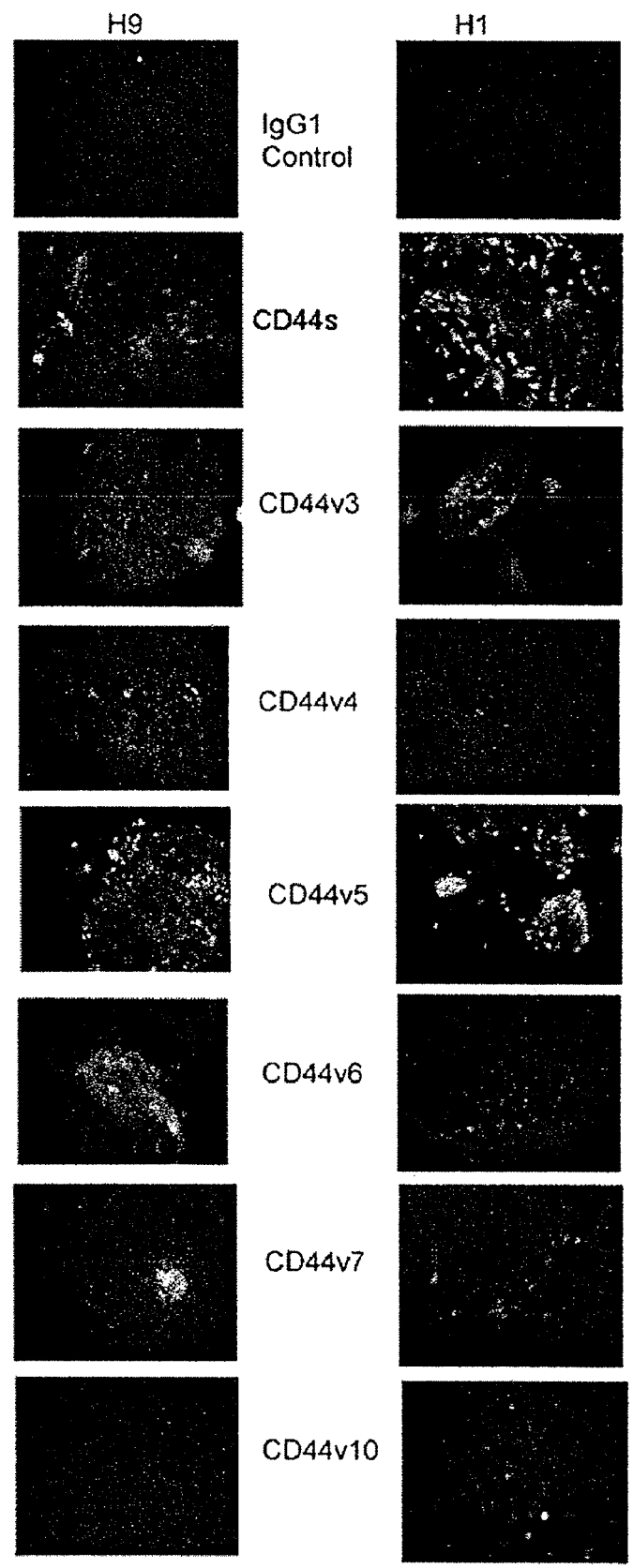

FIG. 7 shows in situ immunofluorescence staining for epitopes of CD44, a major receptor for HA, in H1 and H9 hESCs grown under self-renewing conditions as specified by Xu et al., 2001. Immunostaining suggests that multiple CD44 isoforms are conservatively expressed in different hESC lines. They include isoforms containing epitopes encoded by standard (s) and variant exons v3, 4, 5, 6, 7, and 10. Immunostaining for v3 was predominantly of undifferentiated colony cells that are known to have self-renewing capacity.

Figure 8:
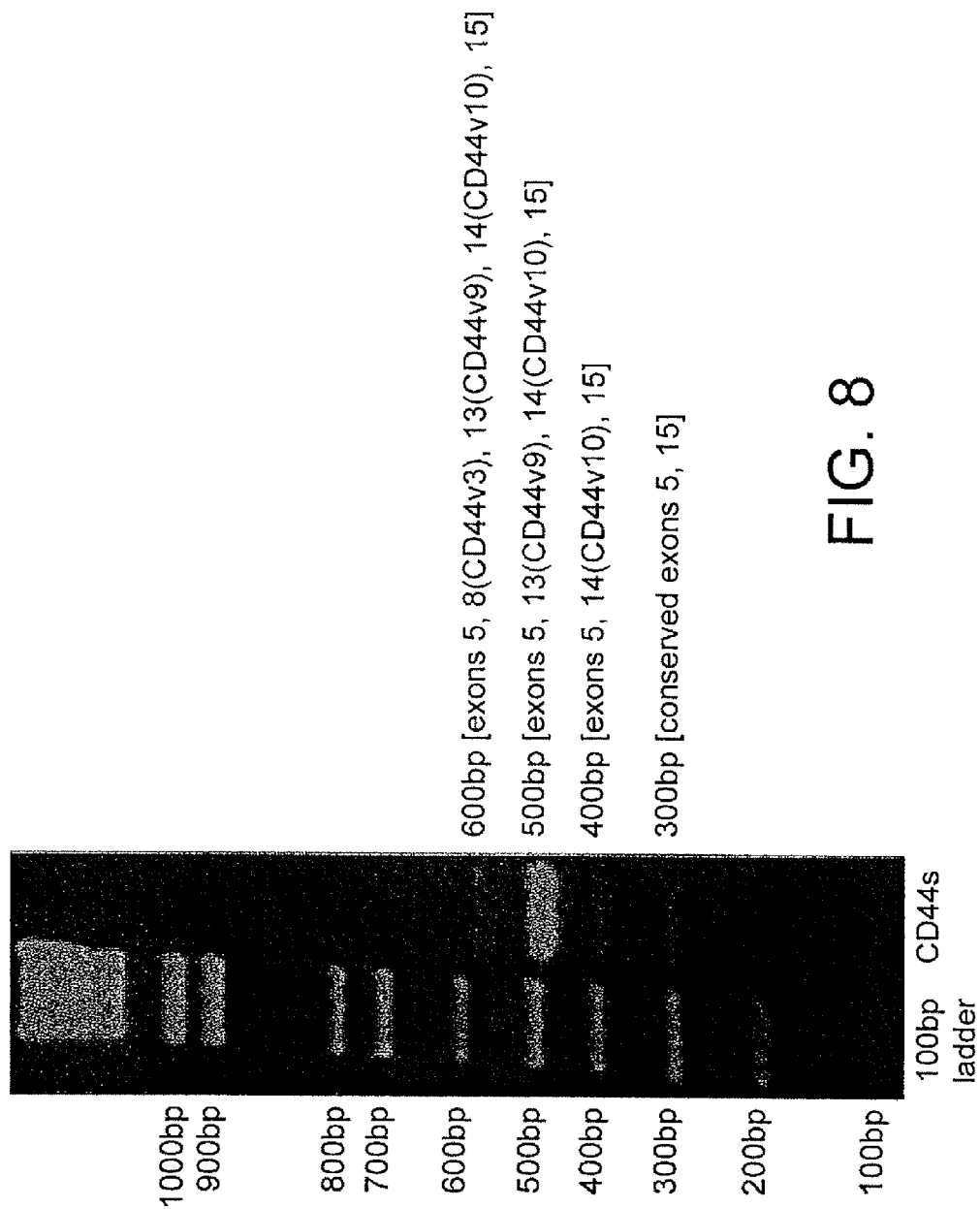

FIG. 8 shows detection by RT-PCR of CD44 isoforms in undifferentiated H1 hESCs grown in self-renewing conditions as described by Xu et al., (2001) using primers to exons 5 and 15 flanking variant extracellular exons. At an RNA level, the predominant isoforms appear to be those which either lack variant exons, or contain variant exons v10, v10 & v9, or v10, v9 & v3

Figure 9:
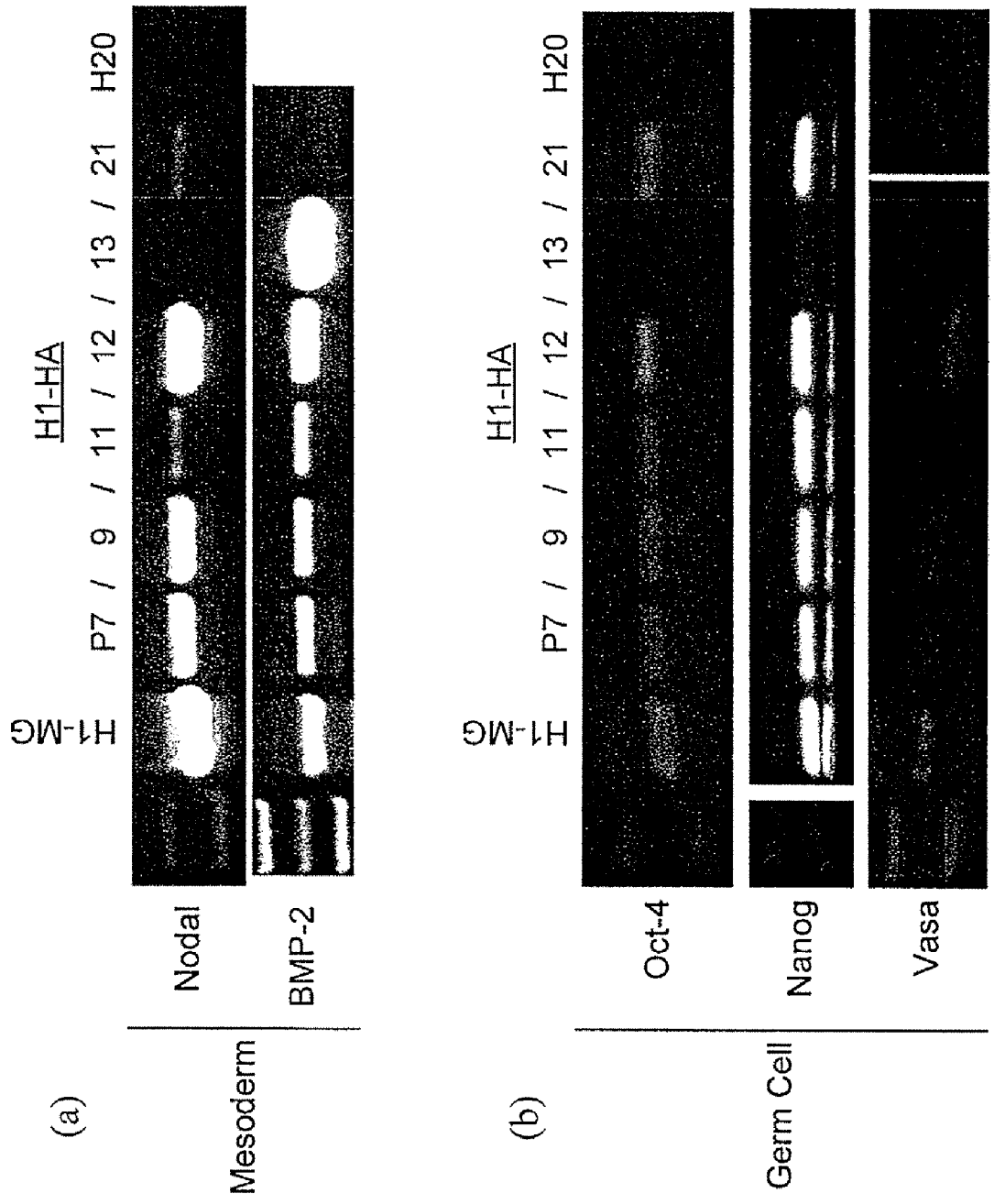

FIG. 9 shows the effect of HA as an hESC substrate. mRNA detection by reverse transcription polymerase chain reaction (RT-PCR) of genetic markers of mesoderm and pluripotency. (a) expression of mesoderm markers Nodal (562 bp) and BMP-2 (586 bp). (b) expression of pluripotency markersOct-4 (126 bp), Nanog (178 bp) and Vasa (238 bp). In both a and b, from left to right: Lane 1 a portion of 100 base pair molecular weight marker showing markers above or below specified products Lane 2 H1 grown in culture conditions maintaining undifferentiated cell self-renewal involving mouse embryo fibroblast conditioned medium supplemented with 4 ng/ml bFGF on a substrate of Matrigel™ (Xu et al., Nat Biotech 2001; 19:971) (i.e. H-MG). Lane 3-8, H1 hESC grown for 7, 9, 11, 12, 13, 21 passages in the media specified in (A) but on substrate of 100 μg/cm2 HA. Lane 9, Water negative control.

Figure 10:
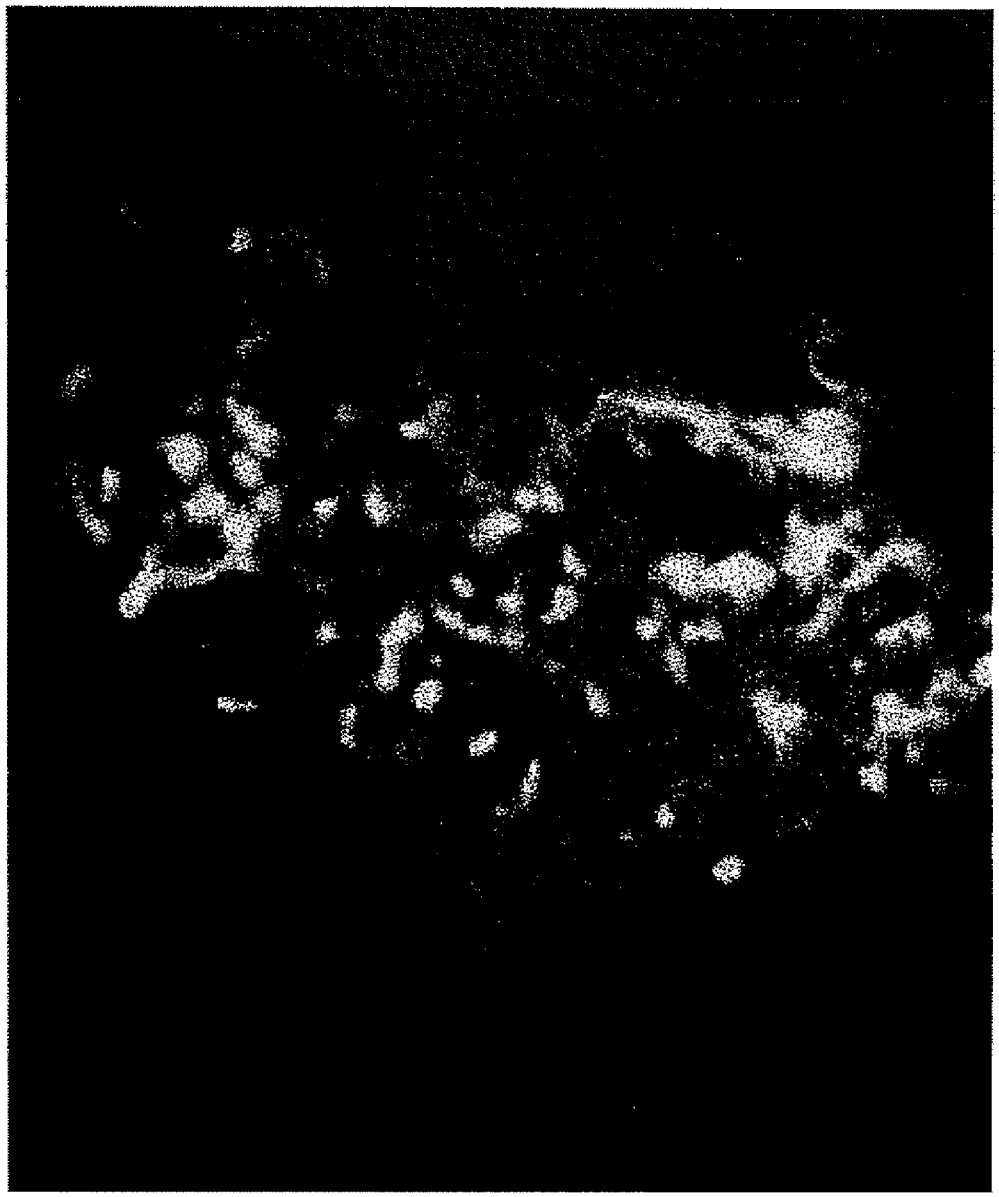

FIG. 10 shows effect of HA as an hESC substrate. Expression of neuronal progenitor marker Nestin post neural induction protocol at p10 as described by Gerard et al., 2005).

Figure 11:
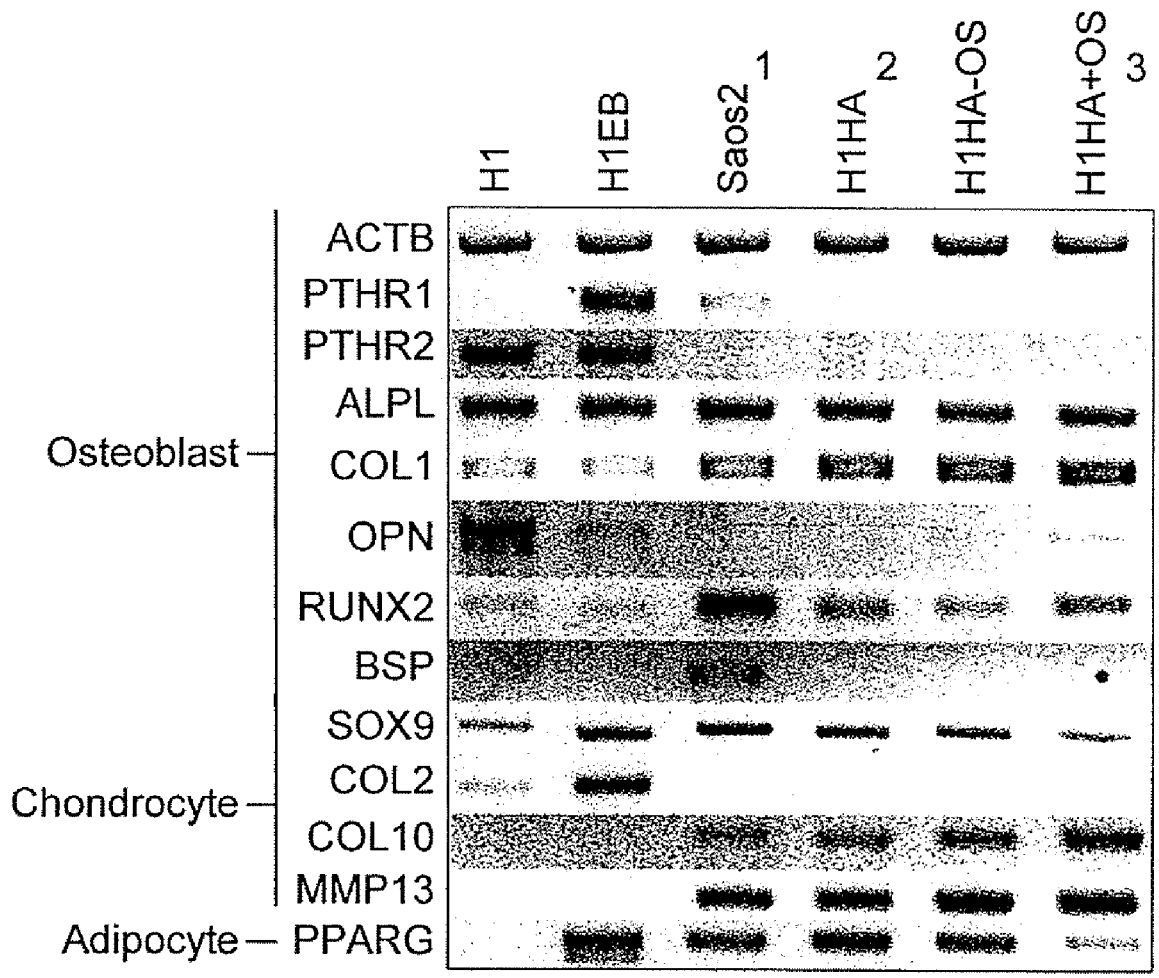

FIG. 11 shows effect of HA as an hESC substrate on mRNA expression of mesoderm lineage markers by RT-PCR. From left to right: Lane 1, H1 hESC grown under conditions that maintain pluripotency (Xu et al., 2001). Lane 2 H1 hESC differentiated as embryoid bodies in suspension culture as per Xu et al., (2001). Lane 3 Adult human osteosarcoma cell line Saos2 treated with OS as per Sottile et al., 2003) for 18 days (superscript 1). Lane 4, H1 hESC grown on HA substrate at 100 μg/cm2 for 10 passages (H1HA-superscript 2). Lane 5-6, HLHA cells grown for 18 days without (lane5) or with (lane 6-superscript 3) OS. Expression patterns suggests that HA treatment causes induction of mesenchymal progenitor cell phenotype with capacity to support fetal endochondrial bone development Abbreviations: OS=Osteogenic supplement; ACTB—β-actin (control); PTIIR1/2—Parathyroid hormone receptor 1/2; ALPL—Alk.phosphatase L (Tissue non-spec.); COL1—Collagen 1 (Major comp. of mesenchyme); OPN—Osteopontin (Secreted Phosphoprotein); RunX2—(CBFA1)/Transcrip. Factor targeting osteocalcin; BSP—Bone Sialo protein (Mature Osteoblast); Sox9—(Transcription factor); Col2—Collagen 2 (Major component of Hyaline cartilage—Chondrocyte; Col10—Collagen 10 (Hypertrophic cartilage @transition to bone); MMP13—Matrix metaloprotein 13r; PPARG-2—peroxisome proliferator-activated receptor-gamma

MATERIALS AND METHODS

HESC Culture

Experiments were performed on both H1 and H9 hESC lines (Thomson et al., 1998). Treatments were replicated in 6 well plates (9.6 cm²/well) seeded at approximately $5\times10^5$, and passaged/split 1:3 at confluence every 4-6 days, depending on the treatment condition. As a reference standard control cultures of hESC lines were maintained as described by Xu et al. (2001) in Mouse Embryo Fibroblast (MEF) Conditioned Medium (CM) composed of 80% KNOCKOUT-Dulbecco's Modified Eagle's Medium (DMEM), 20% KNOCK-OUT serum replacement (KOSR; Invitrogen), 1 mM glutamine, 0.1 mM β-mercaptoethanol, 1% nonessential amino acids, and 4 ng/ml human basic fibroblast growth factor (hbFGF). Cell cultures were normally grown in an atmosphere of 5% $CO_2$ in humidified air (20% $O_2$) at 37° C., and fed fresh MEF CM daily. Cultures were normally passaged by incubation in 200 units/ml Collagenase IV for 5-10 min at 37° C. Alternatively, hESCs were grown in an atmosphere of 5% $CO_2$, 5% $O_2$, and 90% $N_2$ (May 5, 1990), and/or passaged by incubation in Trypsin-EDTA (Invitrogen) for 5-10 min at 37° C.

Embryoid Body Mediated Differentiation

Human ES cells were dissociated into small clumps by treatment for 10 min in 200 Units/Collagenase IV in KO-DMEM at 37° C., and cultured for 4 days in suspension on low cluster plates in embryoid body differentiation (EBD) medium consisting of 80% KO-DMEM, 20% FBS (not heat inactivated), 1 mM L-glutamine, 0.1 mM β-mercaptoethanol, 1% nonessential amino acids. The resulting embryoid bodies were transferred onto glass slide tissue culture chambers coated with 0.5% gelatin @ 0.1 ml/cm$^2$, and cultured for an additional 11 days, feeding every second day.

Induction of Osteogenesis

Osteogenic differentiation was induced as previously described by Sottile et al., (2003). An osteogenic (OS) supplement consisting of 50 μM ascorbic acid phosphate (Wako, Neuss, Germany), 10 mM β-glycerophosphate (Sigma), and 100 nM dexamethasone (Sigma) was added to EBD medium. Cells derived from embryoid bodies (H9 control) or grown previously on HA (H1) for 10 or 20 passages were plated on 0.1% gelatin and treated with EBD medium±OS that was changed every 2 days over the indicated intervals.

HMSC Cell Culture

The hiMSC/c151 immortalised human bone marrow stromal cell line (Okamoto et al., 2002) kindly provided to the McWhir lab by Dr. J. Toguchida (Kyoto University, Japan)—referred to as hMSC) was cultured and expanded as previously described in DMEM containing 10% FCS, L-glutamine and nonessential amino acids.

Tissue Culture Plate Coating

Matrigel™ (Becton Dickinson) diluted 1:30 in cold KO-DMEM was applied as a coating of 0.1 ml per cm$^2$, with coated plates used between 1-7 days of storage at 4° C. Hyaluronate Disaccharide (HD) at 10 μg/ml in PBS, and Hyaluronic acid (HA; 2000 kD purified from Streptococcus sp.) at 100 μg/ml in PBS, were applied as coatings of 0.1 ml per cm$^2$ for 30 min at 4° C., before warming to room temperature, aspiration of excess and transfer of cells.

Flow Cytometry

Single cell suspensions of were prepared by treatment with Trypsin EDTA, resuspended in KO DMEM and aliquoted for each probe to be evaluated. Cells were spun at (11000 g) for 5 min, and resuspended in 50 μl of Blocking Buffer consisting of 40% heat inactivated Rabbit serum (Jackson's Immunosystems, Stratech Scientific Ltd) in Staining Buffer (SB) composed of 2% FCS in PBS and 2 mM EDTA. Cells were blocked for 10-15 min on ice, followed by addition of primary antibody probes at the recommended concentration (see supplementary table 4) and incubation on ice for 30 min. To remove unbound probe, 3 mls of SB were added per group, and decanted after centrifugation at (1300 rpm) # g's for 5 min. When necessary exposure to the requisite dilution of fluorescent probe conjugated secondary antibody was in 100 μl of SB on ice for 30 min in the dark. Unbound probe was removed by addition of 3 ml of PBS, decanted following centrifugation at 1000 g's for 5 min. For immediate assessment on a Becton Dickinson FACSCAN, cells were resuspended in 0.5-11.0 ml of PBS. Otherwise cells were resuspended in 0.5-1 ml of 1% paraformaldehyde (PFA) in PBS, and stored in the dark at 4° C. for assessment within 24 h.

Immunocytochemistry

Cells were plated on either 4 well-glass chambers or microscope slides precoated with Matrigel™ as previously described, and cultured to desired confluence or differentiation. Cells were washed with PBS before fixation in 4% PFA in PBS for 20 min at room temperature. Fix was removed by washing 2×5 min with PBS, and immunostained immediately or after storage in PBS for up to 2 weeks. Cells were blocked with PBS containing 10% Normal Goat Serum and 0.01% Triton-X for 1 h at room temperature. Primary and secondary antibodies at optimised dilutions (see supplementary table) were prepared in PBS containing 1% NGS and 0.01% Triton-X. These were used at room temperature for 1-2 h, with unbound antibody removed by 3×5-10 min washes in PBS at room temperature. Slides were mounted in Vectashield containing Dapi (Cat. No., Supplier, City, Country), and stored at 4° C. in the dark prior to viewing on an Zeiss Axiovert S100 equipped for epifluorescence and digital imaging and analysis.

Reverse Transcription Polymerase Chain Reaction (RT-PCR) Analysis

RNA was isolated using RNAzol and reverse transcribed using a First strand cDNA synthesis kit (Supplier, City, Country) according to manufacturers instructions. Gene-specific PCR was performed in accordance with gene requirements. To quantify the steady state level of mRNA for undifferentiated hESC markers (Oct-4, and Cripto) transcript abundance was measured by quantitative Real-Time RT-PCR using a TaqMan Universal PCR Master Mix protocol for an ABI Prism 7700 Sequence Detection System equipped with version 1.9.1 analysis software. Transcript abundance in experimental treatment groups was first normalised to amplification of 18S rRNA, and then expressed relative to normalised transcript abundance in control undifferentiated HESC culture on MG. Oligonucleotide primers and probes are summarised in supplementary table 2, with TAQMAN used according to manufacturers recommendations (ABI Biosystems: http://www.europe.appliedbiosystems.com).

Osteoblast Staining and Mineralisation Assays

Detection of mineralised nodules by Aliziarin-Red S (Sigma) staining and calcium deposition were as described previously by Sottile et al., 2003. Prior to staining cells were washed twice with calcium- and magnesium-free PBS, followed by fixation in 95% methanol. Fixed cells were incubated with a 1% Alizarin-Red S (Sigma) solution for 10 min, and then washed twice with water. Cell matrix-associated calcium deposition was determined in 96 well plates using the Sigma calcium assay kit (Sigma), in triplicate wells.

Example 1

Capacity of Hyaluronan to Serve as a Soluble Substrate for Human Embryo Stem Cells (hESC) Growth Under culture conditions which maintain hESC self-renewal, hESCs secrete Hyaluronan and express receptors which can bind to it and mediate its effects, most notably Syndecan (CD138) and the Homing-Cell Adhesion Molecule (H-CAM, also known as CD44) (FIG. 1).

FIG. 1(I) shows the results of in situ fluorescence microscopy on undifferentiated hESC H1 (shown) and H9 with a fluorescently-tagged HA-binding protein stains undifferentiated colony (A) and differentiating non-colony cells (A'). Both hESC populations are also positive for the HA-binding proteoglycan syndecan, also known as CD138 (B), and the constitutive isoform of the CD44 receptor lacking variant exons, known as CD44s (C). hESCs treated with fluorescently conjugated secondary antibody alone and imaged digitally at the same settings used for HA-binding proteins exhibit negligible staining (D). Bars equal 10 microns. FIG. 1(II) shows maintenance of H1 (shown) and H9 in MEFCM/MG as described in the methods preserves undifferentiated colony cells (see * in A) whereas plating of both lines on HA (shown) or HD in high (shown) or low oxygen atmosphere, and passaging with Collagenase (shown) or Trypsin, results in differentiation to a fibroblast-like-morphology which proliferate rapidly as a monolayer for over 25 passages. By contrast, growth on plastic alone (C) yields a similar morphology but growth arrest after 5-7 passages. Bars equal 10 microns.

With this insight, the capacity of Hyaluronan was investigated for its ability to serve as a soluble substrate for human embryo stem cells (hESC) growth in bFGF supplemented and feeder cell-conditioned medium that normally supports self-renewal. Culture of both H1 and H9 cell lines on Hyaluronan Disaccharide (HD) or low molecular weight HA (2000 kD) promotes differentiation into a fibroblast-like morphology within 5 passages of growth in a high or low oxygen atmosphere (i.e. 5% CO2 in air (20% O2), or 5% CO2, 5% O2, 90% N2 (May 5, 1990)), with cells dissociated using collagenase or trypsin (FIG. 1).

Co-incident with their differentiation, HA induced cells lose most undifferentiated hESC markers, including SSEA-4, Tra-1-60, Tra-1-80, Oct-4, Cripto, but retain CD-9 (FIG. 2).

FIG. 2(I) shows results using Flow cytometry, undifferentiated H1 (shown) or H9 hESC on MEFCM/MG are +ve for SSEA4, Tra-1-60, Tra-1-81, and CD9, but –ve for SSEA-1 (A). By contrast all cell surface markers, with the exception of CD9, are lost following growth on HA (B, @p11), HD (C, @p11), or untreated plastic (D, @p7). FIG. 2(II) shows results using TAQMAN RT-PCR, the abundance of mRNA transcripts for genes associated with hESC pluripotency, namely Oct-4 and Cripto, are reduced following successive passage (p) on HA or HD, relative to growth on Matrigel™. Return to Matrigel™ does not result in a rise in the expression of these genes.

Unlike hESCs plated on plastic alone that also become fibroblast-like and gradually cease to proliferate after 5-10 passages, HA induced cells grow rapidly as a monolayer for over 25 passages before their arrest. Their ability to form Embryoid bodies (EBs) and indirectly differentiate into adult cells representative of endodermal, mesodermal, and ectodermal lineages, specifically those expressing α-fetoprotein, muscle-specific actin, and β-tubulin III, respectively, is lost by 10 passages on HA or HD (FIG. 3). Despite this HA induced cells retain the capacity to form mineralising osteoblasts, by direct differentiation protocol after a further 10 passages (FIG. 5). In addition, RT-PCR for definitive markers of endoderm and lineages, specifically GATA-6 (meso/endoderm), HNF-3b and HNF-4-a (primitive and definitive endoderm), and PAX-6 and SHH (ectoderm), continued to be expressed at later passages near the time of loss of proliferative potential (FIG. 6). These cells also retained expression of adult mesenchymal markers CD71 and 90 like embryo stem cells, but not CD34 and 45 expressed by hematopoietic cells (FIG. 4). Thus, when provided as a matrix for hESC attachment under media conditions that normally maintain hESC self-renewal, HA induces differentiation of a proliferative and mortal cell population whose potential to form osteoblasts is retained for an extended period. This may benefit strategies for the therapeutic transplantation of osteoblasts by minimising the potential for transmission of teratoma forming undifferentiated cells.

Example 2

Expression of CD44 Isoforms on hESCs

The predominant receptor for HA is CD44, mediating most of its roles in cell attachment, migration, proliferation and differentiation. CD44 is encoded by a single gene expressed as multiple isoforms as a result of alternative splicing and post-translational modifications. Expression of these variant exons can both modulate and be modulated by growth factor ligands and receptors. We have also investigated the expression of CD44 variant (v) exons in human embryo stem cell lines at a protein and mRNA level in order to understand HA signalling pathways affecting stem cells, specifically hESCs. By indirect immunofluorescence microscopy both H1 and H9 hESCs exhibited significant staining above that observed with secondary antibody alone with all antibody probes evaluated that were directed against the standard isoform of CD44 (CD44s) as well as variant exons for v3, 4, 5, 6, 7 and 10. Immunostaining for CD44v3, was predominantly localised to undifferentiated colony cells. (FIG. 7). Using RT-PCR primers to conserved exons which flanked variant extracellular domains for CD44 on H1 mRNA we amplified, subcloned and sequenced four major products of 300 bp [conserved exons 5, 15], 400 bp [exons 5, 14 (v10), 15], 500 bp (exons 5, 13 (v9), 14 (v10), 15) and 600 bp (5, 8 (v3), 13 (v9), 14 (v10), 15). These results indicate that multiple isoforms of CD44 are expressed by undifferentiated hESCs, the predominant of which are those containing the standard exons and no variant exons, or variant exons 10, 9 and 10, or 3, 9 and 10. (FIG. 8).

TABLE 1

Summary of FACS and cytochemical probes.

| Targeted Epitope | Probe type-(Conjugate) | Supplier | Catalogue # | Dilution | Use |
|---|---|---|---|---|---|
| AFP | Mouse monoclonal IgG2a | Sigma-Aldrich | A8452 | 1:500 | FM |
| β-Tubulin | Mouse monoclonal IgG2b | Sigma-Aldrich | T8660 | 1:1000 | FM |
| CD44 (HCAM)* | Mouse monoclonal IgG1 | Santa Cruz | sc-7297 | 1:200 | FM |
| Muscle Actin | Mouse monoclonal IgG1 Kappa | DAKO | M0635 | 1:50 | FM |
| Syndecan | Mouse monoclonal IgG1 | Cymbus | CBL588 | 1:50 | FM |
| Non-specific serum ? | Mouse monoclonal IgG3 | Sigma | M3645 | 1:100 | FACS |
| Non-specific serum ? | Mouse monoclonal IgM | Sigma | M3795 | 1:100 | FACS |
| SSEA1 | IgM | DSHB | MC-480 | 1:5 | FACS |
| SSEA4 | IgG3 | DSHB | MC-813-70 | 15:50 | FACS |
| Tra-1-60 | Mouse monoclonal IgM | Chemicon | MAB 4360 | 1:10 | FACS |

TABLE 1-continued

Summary of FACS and cytochemical probes.

| Targeted Epitope | Probe type-(Conjugate) | Supplier | Catalogue # | Dilution | Use |
|---|---|---|---|---|---|
| Tra-1-81 | Mouse monoclonal IgM | Chemicon | MAB 4381 | 1:20 | FACS |
| CD-9 | Mouse monoclonal IgG1-(PE) | BD Pharmingen | 555372 | 1:5 | FACS |
| Mouse Ig__ | Goat polyclonal IgG-(FITC) | Sigma-Aldrich | F5262 | 1/100 | FM |
| Mouse Ig__ | Donkey polyclonal IgG-(Cy3) | Jackson | 715-095-150 | 1/100 | FM |
| Rabbit Ig__ | Goat polyclonal IgG-(FITC) | Sigma-Aldrich | F9887 | 1/100 | FM |
| Mouse Ig__ | Donkey polyclonal IgG-(TRITC) | Jackson | 715-025-150 | 1/100 | FM |
| Mouse Ig__ | Goat polyclonal IgG-(FITC) | Southern Biotechnologies | 1102-02 | 1/100 | FACS |
| Mouse Ig__ | Goat polyclonal IgG-(PE) | Southern Biotechnologies | 1022-09. | 1/100 | FACS |
| Mouse IgG1 (Kappa) | Rat | BD Pharmingen | 349073 | 1/100 | FACS |
| Non-specific serum ? | IgG1-(PE) | BD Pharmingen | 555749 | 1/100 | FACS |
| Hyaluronan | HA Binding Protein-(FITC) | CalBiochem | 385906 | 1/100 | FM |

TABLE 2

Oligonucleotide Primer Information

| Name | Primer Seq (5'-3') | Accession No. | C DNA posn. | Gen DNA posn. | Spans Intron | Chrom |
|---|---|---|---|---|---|---|
| GATA6 BP for | CCATGACTC CAACTTCCA CC-3' | >gi\|40288196\|ref\|NM_0052 57.3\| | 1803-1822 | 18014909-18014928 | | |
| GATA6 BP rev | ACGGAGGAC GTGACTTCG GGC' | >gi\|40288196\|ref\|NM_0052 57.3\| | 1998-2016 | 18032718-18032736 | YES | |
| HNF-3β for | AGATGGAAG GGCACGAGC' | >gi\|5805393\|gb\|AF176110.1\|AF176110 | 1621-1638 | 22559865-22559882 | | 20 |
| HNF-3β rev | CAGGCCGGC GTTCATGTT | >gi\|5805393\|gb\|AF176110.1\|AF176110 | 2729-2746 | 22558757-22558774 | No | |
| HNF-4α for | CTGCTCGGA GCCACCAAG AGATCCTG | >gi\|1217960\|emb\|Z49825.1\|HSHNF4A | 878-901 | 43732531-43732554 | | |
| HNE-4α rev | ATCATCTGC CCACGTGAT GCTCTGCA' | >gi\|1217960\|emb\|Z49825.1\|HSHNF4A | 1224-1248 | 43738226-43738249 | YES (2) | |
| HSHH for | TTAGCCTAC AAGCAGTTT ATCC | >gi\|663156\|gb\|L38518.1\|HUMSHH | 275-296 | 155021527-155021548 | | 7 |
| HSHH rev | ACTCGTAGT ACACCCAGT CG | >gi\|663156\|gb\|L38518.1\|HUMSHH | 661-686 | 155015972-155015997 | YES | |
| hPAX6 for | AACAGACAC AGCCCTCAC AAACA | gi\|189632\|gb\|M93650.1\|HUMPAX6AN | 1368-1390 | 31779354-31779376 | | 11 |
| HPAX6 rev | CGGGAACTT GAACTGGAA CTGAC | gi\|189632\|gb\|M93650.1\|HUMPAX6AN | 1620-1642 | 31775835-31775957 | YES (2) | |

TABLE 2-continued

Oligonucleotide Primer Information

| Name | Primer Seq (5'-3') | Accession No. | C DNA posn. | Gen DNA posn. | Spans Intron | Chrom |
|---|---|---|---|---|---|---|
| β-actin for | TCACCACCA CGGCCGAGC G | X00351 | 640-658 | | YES | |
| β-actin rev | TCTCCTTCTG CATCCTGTC G | X00351 | 990-971 | | | |
| hOct-4 F | ACATCAAGC TCTGCAGAA AGAAC | NA | | | | |
| hOct-4-R | CTGAATACC TTCCCAAAT AGAACCC | NA | | | | |
| hNanog-F | CAGCTGTGT GTACTCAAT GATAGATTT | NA | | | | |
| h-Nanog-R | ACACCATTG CTATTCGGC CAGTTG | NA | | | | |
| h-Vasa-F | AAGAGAGGC GGCTATCGA GATGGA | NA | | | | |
| h-Vasa-R | CGTTCACTTC CACTGCCAC TTCTG | NA | | | | |
| h-Nodal-F | CGACCAACC ATGCATACA TCC | NA | | | | |
| h-Nodal-R | GTGACTTCA TCCCACCTC CAA | NA | | | | |
| h-BMP2-F | CTTCTAGCG TTGCTGCTT CC | NA | | | | |
| h-BMP2-R | TGCTTGCAT TCTGATTCA CC | NA | | | | |
| TAQMAN OCT for | GAA ACC CAC ACT GCA GCA GA | gi\|18088410\|g b\|BC020712. 1\| | 557-578 | 31239192-31239211 | | |
| TAQMAN OCT rev | CAC ATC CTT CTC GAG CCC A | gi\|18088410\|g b\|BC020712. 1\| | 599-617 | 31238889-31239169 | | |
| TAQMAN OCT Probe | CAG CCA CAT CGC CCA GCA GC | gi\|18088410\|g b\|BC020712. 1\| | 578-597 | 31239190-31239170 | | |
| TAQMAN Cripto for | TGA GCA CGA TGT GCG CA | >gi\|30220\|em b\|X14253.1\|H SCRTPTO | 565-581 | 46581915-46581931 | | Y |
| TAQMAN Cripto rev | TTC TTG GGC AGC CAG GTG | >gi\|302200\|em b\|X14253.1\|H SCRIPTO | 627-610 | 46582057-46582074 | | |
| TAQMAN Cripto Probe | AGA GAA CTG TGG GTC TGT GCC CCA TG | >gi\|30220\|em b\|X14253.1\|H SCRIPTO | 583-608 | 46581933-46582055 | | |

TABLE 3

Primary and secondary antibodies for CD44 screening

| | |
|---|---|
| DF1485 | Santa Cruz IgG1 Mouse monoclonal HCAM (CD44s) |
| AB2081 | Chemicon IgG Rabbit polyclonal (CD44v3) |
| MCA1728 | Serotec IgG1 Mouse monoclonal (CD44v4) |
| MCA1729 | Serotec IgG1 Mouse monoclonal (CD44v5) |
| MCA1730 | Serotec IgG1 Mouse monoclonal (CD44v6) |
| MCA1731 | Serotec IgG1 Mouse monoclonal (CD44v7) |
| MCA1733 | Serotec IgG1 Mouse monoclonal (CD44v10) |
| 555748 | Becton Dickinson Pharmingen IgG1 FITC (neg. control) |
| F9887 | Sigma Anti-Rabbit FITC (for CD44v3 and its negative control) |
| F5262 | Sigma Anti-Mouse FITC (for the rest CD44 variants) |

TABLE 4

Dilutions of antibodies

| | |
|---|---|
| CD44s (HCAM) | 1/100, 2ndary anti-mouse FITC 1/100 |
| CD44v3 | 1/25, 2ndary anti-rabbit FITC 1/100 |
| CD44v4 | 1/100, 2ndary anti-mouse FITC 1/100 |
| CD44v5 | 1/100, 2ndary anti-mouse FITC 1/100 |
| CD44v6 | 1/100, 2ndary anti-mouse FITC 1/100 |
| CD44v7 | 1/100, 2ndary anti-mouse FITC 1/100 |
| CD44v10 | 1/100, 2ndary anti-mouse FITC 1/100 |
| Pre-conjugated IgG1 negative control | 20 μl antibody + 100 μl NGS 1%, no secondary antibody |
| Negative v3 | no primary antibody (100 μl NGS 1%), secondary anti-rabbit FITC 1/100 |

Summary of Results:
1. Characterisation of hESC growth on Low Molecular Wt HA or HD vs. Matrigel in MEF CM/low bFGF culture.
   a. Both H1 and H9 react with and express HA-binding proteins (FIG. 1I).
      i. Fluorescent HA-Binding protein staining reflects endogenous HA.
      ii HA-binding proteoglycan (Syndecan, CD138) expressed by colony and differentiating cells.
      iii Constitutive form of predominant HA receptor (CD44s) expressed by both colony and differentiating cells.
   b. For both H1 & H9, growth on HA/HD promotes differentiation to fibroblast-like morphology, which is irreversible after 5-7 passages (FIG. 1 II).
      i Differentiation occurs regardless of whether in low oxygen or high oxygen (5% CO$_2$ in air) tension, and method of cell dissociation (collagenase vs. trypsin)—data not shown.
      ii Unlike hESC plated on plastic alone that also differentiate into fibroblast morphology and cease to proliferate by p10, HA induced cells proliferate until approximately p27.
   c. Karyotype of HA induced cells is preserved until end of proliferative life (data not shown).
   d. Differentiation is characterised by loss of most undifferentiated surface markers by FACS (i.e. SSEA4, Tra-1-60, Tra-1-81, but not CD9) & genetic markers by TAQ-MAN markers (i.e. Oct-4, Cripto, hTert, podocalyxin, GRP-R) (FIG. 2).
   e. HA induced cells lose ability to form embryoid bodies and indirect differentiation by approximately p10 (FIG. 3).
   f. HA induced fibroblasts and undifferentiated hESC resemble human bone marrow stromal cells in that they are +ve for CD71, CD90 & CD44 and negative for CD34 and 45 (FIG. 4).
   g. After loss of EB forming capacity, HA induced cells respond to osteogenic factors to form mineralising osteoblasts (FIG. 5).

Example 3

Expression of Lineage Markers in hESCs Cultured on HA

The effect of HA as an hESC substrate on expression of lineage markers can be seen as follows. Mesoderm markers Nodal and BMP-2 are shown in FIG. 9(a) and pluripotency cell markers Oct-4, Nanog and Vasa in FIG. 9(b). Further evidence of mesodermal marker expression is shown in FIG. 10 where the neuronal progenitor cell marker Nestin is expressed at passage 10, FIG. 11 shows a more comprehensive survey of mesodermal marker expression in hESCs cultured on HA as a substrate. Expression suggests that HA induction of mesenchymal progenitor cells and fetal endochondrial bone development (vs intramem in adult).

The markers shown to be expressed include ACTB—β-actin (control); PTBR1/2—Parathyroid hormone receptor 1/2; ALPL—Alk.phosphatase L (Tissue non-spec.); COL1—Collagen 1 (Major comp. of mesenchyme); OPN—Osteopontin (Secreted Phosphoprotein); RunX2—(CBFA1)/Transcrip. Factor targeting osteocalcin; BSP—Bone Sialo protein (Mature Osteoblast); Sox9—(Transcription factor); Col2—Collagen 2 (Major component of Hyaline cartilage—Chondrocyte; Col10—Collagen 10 (Hypertrophic cartilage @transition to bone); MMP13—Matrix metaloprotein 13r; PPARG-2—peroxisome proliferator-activated receptor-gamma

REFERENCES

Amit M, et al., 2003, Biol Reprod. 68(6):2150-6
Amit M, et al., 2004, Biol Reprod. 70(3):837-45
Brown J. and Papaioannou, V. (1993) Development 117: 483-492.
Camenisch T. et al., (2000) J Clin Invest 106: 349-60.
Camenisch T. et al., (2002) Nat Med 8: 850-5.
Chung Y. et al., Nature. 2006 Jan. 12; 439(7073):216-9
Conley B J, et al., 2004, Int J Biochem Cell Biol. 36(4):555-67
Gerrard L et al., Stem Cells 2005:23:1234-41
Hardingham and Muir, Biochim Biophys Acta. 1972 Sep. 15; 279(2):401-5.
Hardwick et al., J. Cell Biol. 1992 June; 117(6):1343-50
Isacke C. and Yarwood II. (2002) Int J Biochem Cell Biol 34: 718-21.
Itskovitz-Eldor J, et al., 2000, Mol. Med. 6(2):88-95
Jalkanan et al., Annu Rev Med. 1987; 38:467-76
Keller G M, 1995, Curr Opin Cell Biol. 7(6):862-9
Locci P. et al., (1995) Cell Tissue Res 281: 317-24
Meissner & Jaenisch Nature, 2006, 439, 212-215
Okamoto et al., 2002; Biochem. Biophys. Res. Commun. 295: 354-361
Radomsky M L et al., (1998) Clin Orthop 355:S283-93.
Richards M, et al., 2002, Nat. Biotechnol. 20(9):933-6
Rosler E S, et al., 2004, Dev Dyn. 2004 February; 229(2): 259-74
Schumacher A, et al., 2003 Mol Cell Neurosci. 23(4):669-80
Sottile et al., (2003; Cloning & stem cells 5: 149
Uchida N, et al., 2000, Proc Natl Acad Sci USA. 97(26): 14720-5

Verfaillie C, Trends in Cell Biology 2002; 12, 502-8
Xu et al., 2001, Nature Biotech 19, 971
Zhang S C, et al., 1998, J Neurocytol. 27(7):475-89

The invention claimed is:

1. A method for the differentiation of mammalian pluripotent stem (PS) cells into mortal multi-lineage progenitor cells, comprising:
obtaining isolated PS cells; and
culturing the PS cells in the presence of hyaluronan to induce differentiation of the cells,
wherein said culturing results in the differentiation of the PS cells into mortal multi-lineage progenitor cells expressing CD71, CD90, and CD44 and lacking expression of CD34 and CD45.

2. The method of claim 1, wherein the mortal multi-lineage progenitor cells are a population of mesenchymal stem cells.

3. The method of claim 1, wherein the mortal multi-lineage progenitor cells form cells of the mesodermal lineage.

4. The method of claim 3, wherein the cells of the mesodermal lineage form osteoblasts.

5. The method of claim 1, wherein the mortal multi-lineage progenitor cells form cells of the endodermal lineage.

6. The method of claim 1, wherein the mortal multi-lineage progenitor cells form cells of the ectodermal lineage.

7. The method of claim 6, wherein the cells of the ectodermal lineage form neuronal progenitors.

8. The method of claim 1, wherein the PS cells are embryonic pluripotent stem cells.

9. The method of claim 1, wherein the PS cells are adult pluripotent stem cells.

10. The method of claim 1, wherein the PS cells are selected from human and non-human primate, ungulate, ruminant and rodent PS cells.

11. The method of claim 1, wherein the multi-lineage progenitor cells are adult human mesenchymal cells.

12. The method of claim 1, further comprising transplantating the mortal multi-lineage progenitor cells into a patient.

13. The method of claim 1, wherein the PS cells are a human embryonic stem cell line.

14. The method of claim 1, comprising culturing the PS cells on a coating of hyaluronan.

15. The method of claim 1, wherein the mortal multi-lineage progenitor cells express CD105.

16. The method of claim 1, wherein the mortal multi-lineage progenitor cells express Stro-1.

17. The method of claim 15, wherein the mortal multi-lineage progenitor cells express Stro-1.

* * * * *